(12) United States Patent
Abe et al.

(10) Patent No.: US 11,191,520 B2
(45) Date of Patent: Dec. 7, 2021

(54) ULTRASONIC DIAGNOSTIC APPARATUS, IMAGE PROCESSING APPARATUS, AND IMAGE PROCESSING METHOD

(71) Applicant: Toshiba Medical Systems Corporation, Otawara (JP)

(72) Inventors: Yasuhiko Abe, Otawara (JP); Shogo Fukuda, Kawasaki (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 509 days.

(21) Appl. No.: 15/457,257

(22) Filed: Mar. 13, 2017

(65) Prior Publication Data
US 2017/0265843 A1 Sep. 21, 2017

(30) Foreign Application Priority Data

Mar. 17, 2016 (JP) .............................. JP2016-054235
Mar. 7, 2017 (JP) .............................. JP2017-042831

(51) Int. Cl.
*A61B 5/0402* (2006.01)
*A61B 8/00* (2006.01)
(Continued)

(52) U.S. Cl.
CPC ................ *A61B 8/14* (2013.01); *A61B 5/318* (2021.01); *A61B 8/0883* (2013.01); *A61B 8/461* (2013.01);
(Continued)

(58) Field of Classification Search
None
See application file for complete search history.

(56) References Cited

U.S. PATENT DOCUMENTS

2008/0253628 A1* 10/2008 Matsue ................. G06F 19/321
382/128
2008/0262814 A1* 10/2008 Zheng ..................... G06F 19/34
703/11
(Continued)

FOREIGN PATENT DOCUMENTS

CN  101317773 A  12/2008
CN  102523733 A  6/2012
(Continued)

OTHER PUBLICATIONS

Matthews R., Cardiology Definitions: Anatomy of the Heart, pp. 1-92 (Year: 2006).*

(Continued)

*Primary Examiner* — Jonathan Cwern
*Assistant Examiner* — Amal Aly Farag
(74) *Attorney, Agent, or Firm* — Oblon, McClelland, Maier & Neustadt, L.L.P.

(57) ABSTRACT

An ultrasonic diagnostic apparatus according to an embodiment includes an ultrasonic probe and processing circuitry. The ultrasonic probe collects reflected wave data in a time series manner from a region of a subject in motion. The processing circuitry generates time-series volume data from the reflected wave data collected by the ultrasonic probe. The processing circuitry calculates at least either of volume information and motion information on a region of interest of the subject by performing processing including tracking using the volume data. The processing circuitry sets one or more feature positions that represent anatomical features in the region of interest. The processing circuitry displays an MPR image that passes through at least one of the feature positions. The processing circuitry outputs at least either of the volume information and the motion information that includes the feature positions as boundaries.

9 Claims, 10 Drawing Sheets

(51) Int. Cl.
*A61B 8/08* (2006.01)
*A61B 8/14* (2006.01)
*A61B 5/318* (2021.01)

(52) U.S. Cl.
CPC .............. *A61B 8/467* (2013.01); *A61B 8/483* (2013.01); *A61B 8/488* (2013.01); *A61B 8/5207* (2013.01)

(56) References Cited

U.S. PATENT DOCUMENTS

| | | | | |
|---|---|---|---|---|
| 2008/0304730 | A1* | 12/2008 | Abe | A61B 8/08 382/131 |
| 2010/0041992 | A1 | 2/2010 | Ohuchi et al. | |
| 2010/0185094 | A1 | 7/2010 | Hamada et al. | |
| 2011/0144495 | A1* | 6/2011 | Wilkening | A61B 8/0883 600/443 |
| 2011/0176711 | A1* | 7/2011 | Bocirnea | G06T 19/00 382/128 |
| 2011/0301462 | A1 | 12/2011 | Hashimoto | |
| 2012/0165674 | A1* | 6/2012 | Abe | A61B 8/0883 600/443 |
| 2013/0324850 | A1* | 12/2013 | Petruzzelli | A61B 8/467 600/443 |

FOREIGN PATENT DOCUMENTS

| | | |
|---|---|---|
| CN | 103513920 A | 1/2014 |
| JP | 2005-169070 | 6/2005 |
| JP | 2007-68724 | 3/2007 |
| JP | 2010-42151 | 2/2010 |
| JP | 2010-167032 | 8/2010 |
| JP | 2013-188417 A | 9/2013 |
| JP | 2015-213745 A | 12/2015 |

OTHER PUBLICATIONS

Osamu Igawa "Practice and Anatomical Knowledge of Alternative Pacing", Saitama Society of Pacing and Electrophysiology: Therapeutic Research, vol. 31, No. 2, 2010, 12 pages (with Computer Generated English Translation).

Office Action issued Aug. 19, 2020 in corresponding Chinese Patent Application No. 2020081401990910.

Heart and Blood Vessel Ultrasound Biomechanics (In Chinese with English Translation).

Office Action dated Nov. 24, 2020 in Japanese Patent Application No. 2017-042831.

Chinese Office Action dated Apr. 6, 2021 in Patent Application No. 201710152968.X, 5 pages.

* cited by examiner

ULTRASONIC DIAGNOSTIC APPARATUS, IMAGE PROCESSING APPARATUS, AND IMAGE PROCESSING METHOD

CROSS-REFERENCE TO RELATED APPLICATIONS

This application is based upon and claims the benefit of priority from Japanese Patent Application No. 2016-054235, filed on Mar. 17, 2016; and Japanese Patent Application No. 2017-042831, filed on Mar. 7, 2017, the entire contents of which are incorporated herein by reference.

FIELD

Embodiments described herein relate generally to an ultrasonic diagnostic apparatus, an image processing apparatus, and an image processing method.

BACKGROUND

To objectively and quantitatively evaluate a function of a region (such as an organ) of a subject, various techniques have conventionally been developed that analyze image data obtained by capturing the region. For example, to evaluate a cardiac function, a technique for an ultrasonic diagnostic apparatus has been developed that calculates motion information on motion of heart walls. Specifically, the ultrasonic diagnostic apparatus performs a tracking process including local pattern matching of the heart walls on three-dimensional ultrasonic image data of the heart collected in a time series manner, and estimates the motion information from, for example, displacements and distortions of the heart walls. The ultrasonic diagnostic apparatus performs a rendering process to generate an image of, for example, a heart cavity (or, for example, a ventricular wall or an atrial wall) included in a region of interest set by an operator, and displays the image after converting luminance values according to the estimated motion information into colors.

DETAILED DESCRIPTION

An ultrasonic diagnostic apparatus according to embodiments includes an ultrasonic probe and processing circuitry. The ultrasonic probe collects reflected wave data in a time series manner from a region of a subject in motion. The processing circuitry generates time-series volume data from the reflected wave data collected by the ultrasonic probe. The processing circuitry uses the volume data and performs processing including tracking to calculate at least either of volume information and motion information on a region of interest (hereinafter, abbreviated as ROI) of the subject. The processing circuitry sets at least one feature position that represents an anatomical feature in the ROI. The processing circuitry displays a multiplanar reconstruction (MPR) image that passes through at least one such feature position. The processing circuitry outputs at least either of the above-mentioned pieces of information that includes the feature position as a boundary. The following describes the ultrasonic diagnostic apparatus, an image processing apparatus, and an image processing program according to the embodiments, with reference to the drawings.

Although the following describes cases where the embodiments are applied to the ultrasonic diagnostic apparatus, the embodiments are not limited to such oases. The embodiments can also be applied to, for example, medical image diagnostic apparatuses other than the ultrasonic diagnostic apparatus and medical image processing apparatuses, such as workstations. Examples of the applicable medical image diagnostic apparatuses include, but are not limited to, X-ray diagnostic apparatuses, X-ray computed tomography (CT) apparatuses, magnetic resonance imaging (MRI) apparatuses, single photon emission computed tomography (SPECT) apparatuses, positron emission tomography (PET) apparatuses, SPECT-CT apparatuses in each of which a SPECT apparatus and an X-ray CT apparatus are integrated with each other, PET-CT apparatuses in each of which a PET apparatus and an X-ray CT apparatus are integrated with each other, PET-MRI apparatuses in each of which a PET apparatus and an MRI apparatus are integrated with each other, and apparatus groups each including a plurality of such apparatuses.

First Embodiment

Figure 1:
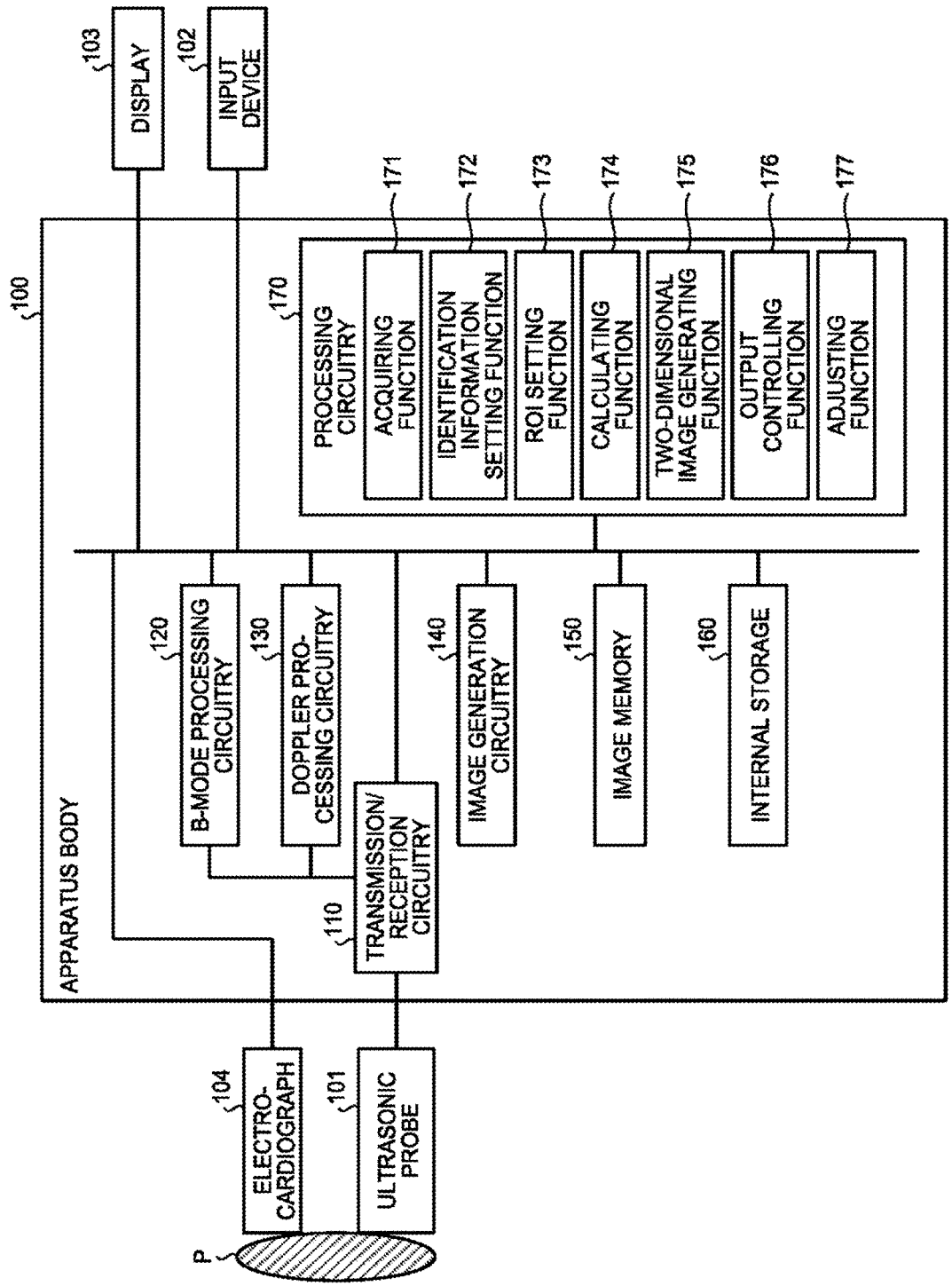
FIG. 1 is a block diagram illustrating a configuration example of an ultrasonic diagnostic apparatus according to a first embodiment.

FIG. 1 is a block diagram illustrating a configuration example of an ultrasonic diagnostic apparatus 1 according to a first embodiment. As illustrated in FIG. 1, the ultrasonic diagnostic apparatus 1 according to the first embodiment includes an apparatus body 100, an ultrasonic probe 101, an input device 102, a display 103, and an electrocardiograph 104. The ultrasonic probe 101, the input device 102, the display 103, and the electrocardiograph 104 are connected to the apparatus body 100 so as to be capable of communicating therewith.

The ultrasonic probe 101 includes a plurality of piezoelectric transducer elements, which generate ultrasonic waves based on a drive signal supplied from transmission/reception circuitry 110 included in the apparatus body 100. The ultrasonic probe 101 receives waves reflected from a subject P and converts them to electrical signals. The ultrasonic probe 101 includes, for example, an alignment layer provided on the piezoelectric transducer elements and a backing material that prevents the ultrasonic waves from propagating backward from the piezoelectric transducer elements. The ultrasonic probe 101 is detachably connected to the apparatus body 100.

When the ultrasonic waves are transmitted from the ultrasonic probe 101 to the subject P, the transmitted ultrasonic waves are successively reflected by a discontinuous plane of acoustic impedance in a body tissue of the subject P, and are received as reflected wave signal by the piezoelectric transducer elements included in the ultrasonic probe 101. The amplitude of each of the received reflected wave signals depends on the difference in the acoustic impedance in the discontinuous plane that reflects the ultrasonic waves. When the transmitted ultrasonic pulses are reflected on a surface of, for example, a moving bloodstream or a heart wall, the reflected wave signals are subjected to a frequency shift due to a Doppler effect depending on a velocity component of the moving body with respect to the direction of transmission of the ultrasonic waves.

In the present embodiment, for three-dimensional scanning of the subject P, for example, a mechanical four-dimensional (4D) probe or a two-dimensional (2D) array probe is connected as the ultrasonic probe 101 to the apparatus body 100. The mechanical 4D probe can perform two-dimensional scanning by using a plurality of piezoelectric transducer elements arranged in a line, such as a one-dimensional (1D) array probe, and can also perform three-dimensional scanning by oscillating a plurality of piezoelectric transducer elements at a certain angle (oscillation angle). The 2D array probe can perform the three-dimensional scanning by using a plurality of piezoelectric transducer elements arranged in a matrix, and can also perform the two-dimensional scanning by transmitting and receiving the ultrasonic waves in a focused manner.

The input device 102 includes, for example, a mouse, a keyboard, buttons, panel switches, a touch command screen, a foot switch, a trackball, and a joystick. The input device 102 receives various setting requests from an operator of the ultrasonic diagnostic apparatus 1, and transfers the received various setting requests to the apparatus body 100.

The display 103 displays a graphical user interface (GUI) for the operator of the ultrasonic diagnostic apparatus 1 to enter the various setting requests using the input device 102, and displays, for example, ultrasonic image data generated in the apparatus body 100. The display 103 displays various messages to notify the operator of processing statuses of the apparatus body 100. The display 103 includes a speaker and can output sounds. The speaker of the display 103 outputs, for example, a predetermined sound, such as a beep sound, to notify the operator of a processing status of the apparatus body 100.

The electrocardiograph 104 acquires an electrocardiogram (ECG) of the subject P as a biosignal of the subject P. The electrocardiograph 104 transmits the acquired ECG to the apparatus body 100. In the present embodiment, a case will be described where the electrocardiograph 104 is used as a device for acquiring information on a cardiac phase of the heart of the subject P. The embodiments are, however, not limited to this case.

The apparatus body 100 is an apparatus that generates the ultrasonic image data based on the reflected wave signals received by the ultrasonic probe 101. The apparatus body 100 illustrated in FIG. 1 is an apparatus that can generate three-dimensional ultrasonic image data based on three-dimensional reflected wave data received by the ultrasonic probe 101. The three-dimensional ultrasonic image data is an example of "three-dimensional medical image data" or "volume data".

As illustrated in FIG. 1, the apparatus body 100 includes the transmission/reception circuitry 110, B-mode processing circuitry 120, Doppler processing circuitry 130, image generation circuitry 140, an image memory 150, an internal storage 160, and processing circuitry 170. The transmission/reception circuitry 110, the B-mode processing circuitry 120, the Doppler processing circuitry 130, the image generation circuitry 140, the image memory 150, the internal storage 160, and the processing circuitry 170 are connected to one another so as to be capable of communicating with one another.

The transmission/reception circuitry 110 includes, for example, a pulse generator, a transmission delay unit, and a pulser, and supplies the drive signal to the ultrasonic probe 101. The pulse generator repetitively generates rate pulses for forming a transmission ultrasonic wave at a certain rate frequency. The transmission delay unit gives each of the rate pulses generated by the pulse generator a delay time for each of the piezoelectric transducer elements necessary to focus the ultrasonic waves generated from the ultrasonic probe 101 into beam-like waves and to determine transmission directivity. The pulsar applies the drive signal (drive pulses) to the ultrasonic probe 101 at timing based on the rate pulses. In other words, the transmission delay unit changes the delay time given to each of the rate pulses so as to adjust the directions of transmission of the ultrasonic waves transmitted from the piezoelectric transducer element surfaces to any directions.

The transmission/reception circuitry 110 has a function that can instantly change a transmission frequency, a transmission drive voltage, and the like in order to perform a predetermined scan sequence based on an instruction of the processing circuitry 170 (to be described later). The change in the transmission drive voltage is specifically achieved by a linear amplifier type oscillator circuit that can instantly change the value thereof, or by a mechanism that electrically switches between a plurality of power supply units.

The transmission/reception circuitry 110 includes, for example, a preamplifier, an analog/digital (A/D) converter, a reception delay unit, and an adder, and applies various types of processing to the reflected wave signals received by the ultrasonic probe 101 to generate reflected wave data. The preamplifier amplifies the reflected wave signals on a channel-by-channel basis. The A/D converter applies A/D conversion to the amplified reflected wave signals. The reception delay unit gives the A/D converted signals a delay time necessary to determine reception directivity. The adder applies addition processing to the reflected wave signals having been processed by the reception delay unit to generate the reflected wave data. The addition processing by the adder enhances reflection components from a direction corresponding to the reception directivity of the reflected wave signals. The reception directivity and the transmission directivity form overall beams of the ultrasonic transmission and reception.

To scan a three-dimensional area of the subject P, the transmission/reception circuitry 110 causes the ultrasonic probe 101 to transmit ultrasonic beams in three dimensional directions. The transmission/reception circuitry 110 generates the three-dimensional ultrasonic image data from the reflected wave signals received by the ultrasonic probe 101.

The form of output signals from the transmission/reception circuitry 110 can be selected from various forms, such as a form of signals called radio frequency (RF) signals that include phase information and a form of amplitude information obtained after envelope detection processing is performed.

The B-mode processing circuitry 120 receives the reflected wave data from the transmission/reception circuitry 110, and applies, for example, logarithmic amplification and the envelope detection processing to the reflected wave data to generate data (B-mode data) that represents signal intensities as levels of luminance.

The Doppler processing circuitry 130 applies frequency analysis to velocity information obtained from the reflected wave data received from the transmission/reception circuitry 110, and extracts echo components of bloodstreams, tissues, and a contrast medium caused by the Doppler effect to generate data (Doppler data) representing moving body information, such as velocities, variances, and power, extracted at multiple points.

The B-mode processing circuitry 120 and the Doppler processing circuitry 130 illustrated in FIG. 1 can process both the two-dimensional reflected wave data and the three-dimensional reflected wave data. Specifically, the B-mode processing circuitry 120 generates two-dimensional B-mode data from the two-dimensional reflected wave data and three-dimensional B-mode data from the three-dimensional reflected wave data, and the Doppler processing circuitry 130 generates two-dimensional Doppler data from the two-dimensional reflected wave data and three-dimensional Doppler data from the three-dimensional reflected wave data.

The image generation circuitry 140 generates the ultrasonic image data from the data generated by the B-mode processing circuitry 120 and the Doppler processing circuitry 130. Specifically, the image generation circuitry 140 generates two-dimensional B-mode image data representing the intensity of the reflected waves as luminance from the two-dimensional B-mode data generated by the B-mode processing circuitry 120, and the image generation circuitry 140 also generates two-dimensional Doppler image data representing the moving body information from the two-dimensional Doppler data generated by the Doppler processing circuitry 130. The two-dimensional Doppler image data is a velocity image, a variance image, a power image, or a combined image thereof. The image generation circuitry 140 can generate M-mode image data from time-series data of the B-mode data on one scanning line generated by the B-mode processing circuitry 120. The image generation circuitry 140 can also generate a Doppler waveform obtained by plotting the velocity information on a bloodstream or a tissue in a time-series manner, from the Doppler data generated by the Doppler processing circuitry 130.

The image generation circuitry 140 performs scan conversion to convert a scanning line signal string of the ultrasonic scanning into a scanning line signal string in a video format represented by television or the like, and thus generates ultrasonic image data for display. Specifically, the image generation circuitry 140 performs coordinate transformation according to the mode of the ultrasonic scanning by the ultrasonic probe 101 to generate the ultrasonic image data for display. The image generation circuitry 140 also performs various types of image processing other than the scan conversion, such as image processing smoothing processing) of regenerating an image having an average luminance value by using a plurality of image frames after being scan-converted and/or image processing (edge reinforcement processing) that uses a differential filter in an image. The image generation circuitry 140 combines the ultrasonic image data with, for example, text information on various parameters, scales, and body marks.

That is to say, the B-mode data and the Doppler data are the ultrasonic image data before being processed by the scan conversion processing, and the data generated by the image generation circuitry 140 is the ultrasonic image data for display after being processed by the scan conversion processing. The B-mode data and the Doppler data are also called raw data.

Moreover, the image generation circuitry 140 applies coordinate transformation to the three-dimensional B-mode data generated by the B-mode processing circuitry 120 so as to generate three-dimensional B-mode image data. The image generation circuitry 140 also applies coordinate transformation to the three-dimensional Doppler data generated by the Doppler processing circuitry 130 so as to generate three-dimensional Doppler image data. In other words, the image generation circuitry 140 generates the three-dimensional B-mode image data and the three-dimensional Doppler image data as the three-dimensional ultrasonic image data (volume data).

Furthermore, the image generation circuitry 140 applies rendering processing to the volume data to generate various types of two-dimensional image data for displaying the volume data on the display 103. Examples of the rendering processing performed by the image generation circuitry 140 include, but are not limited to, processing of using a multi-planer reconstruction (MPR) method to generate MPR image data from the volume data, processing of applying curved MPR to the volume data, processing of applying maximum intensity projection to the volume data, volume rendering (PR) processing, and surface rendering (SR) processing.

The image memory 150 is a memory that stores the image data for display generated by the image generation circuitry 140. The image memory 150 can also store the data generated by the B-mode processing circuitry 120 and the Doppler processing circuitry 130. The B-mode data and the Doppler data stored in the image memory 150 can be called, for example, by the operator after diagnosis, and are converted into the ultrasonic image data for display through the image generation circuitry 140.

The image generation circuitry 140 stores the ultrasonic image data and time of the ultrasonic scanning that has been performed to generate the ultrasonic image data in the image memory 150 in association with the ECG transmitted from the electrocardiograph 104. The processing circuitry 170 (to be described later) can acquire, by referring to the data stored in the image memory 150, the cardiac phase during the ultrasonic scanning that has been performed to generate the ultrasonic image data.

The internal storage 160 stores control programs for performing the ultrasonic transmission and reception, the image processing, and the display processing, diagnostic information (such as patients' IDs and doctors' opinions), and carious types of data, such as diagnostic protocols and various body marks. The internal storage 160 is also used for keeping the image data stored in the image memory 150, as needed. The data stored in the internal storage 160 can be transferred to an external device through an interface (not illustrated). Examples of the external device include, but are not limited to, a personal computer (PC) used by a doctor who performs image diagnosis, a storage medium, such as a compact disc (CD) or a digital versatile disc (DVD), and a printer.

The processing circuitry 170 controls overall processing of the ultrasonic diagnostic apparatus 1. Specifically, the processing circuitry 170 controls the processing of the transmission/reception circuitry 110, the B-mode processing circuitry 120, the Doppler processing circuitry 130, and the image generation circuitry 140 based on the various setting requests entered by the operator through the input device 102 and on the various control programs and the various types of data read from the internal storage 160. The processing circuitry 170 performs control so as to display the ultrasonic image data for display stored in the image memory 150 or the internal storage 160 on the display 103.

The processing circuitry 170 performs an acquiring function 171, an identification information setting function 172, an ROI setting function 173, a calculating function 174, a two-dimensional image generating function 175, an output controlling function 176, and an adjusting function 177. The processing details of the acquiring function 171, the identification information setting function 172, the ROI setting function 173, the calculating function 174, the two-dimensional image generating function 175, the output controlling function 176, and the adjusting function 177 performed by the processing circuitry 170 will be described later.

The internal storage 160 stores the processing functions performed by the acquiring function 171, the identification information setting function 172, the ROI setting function 173, the calculating function 174, the two-dimensional image generating function 175, the output controlling function 176, and the adjusting function 177 serving as components of the processing circuitry 170 illustrated in FIG. 1, in the form of programs executable by a computer. The processing circuitry 170 is a processor that reads out the programs from the internal storage 160 and executes them to perform the functions corresponding to the programs. In other words, once having read out the programs, the processing circuitry 170 has the functions illustrated inside the processing circuitry 170 of FIG. 1.

The present embodiment will be described on the assumption that the single processing circuitry 170 performs the processing functions to be described below. However, a plurality of independent processors may be combined to constitute a processing circuit, and each of the processors may execute corresponding one of the programs to perform the function thereof.

The term "processor" used in the description above refers to, for example, a central processing unit (CPU), a graphics processing unit (GPU), or a circuit, such as an application specific integrated circuit (ASIC) or a programmable logic device (such as a simple programmable logic device (SPLD), a complex programmable logic device (CPLD), or a field-programmable gate array (FPGA)). The processor reads out the program stored in the internal storage 160 and executes it to perform the function thereof. The program may be directly embedded in the circuit of the processor, instead of being stored in the internal storage 160. In this case, the processor reads out the program embedded in the circuit thereof and executes it to perform the function thereof. The processors of the present embodiment are not limited to the case of being configured as single circuits on a processor-by-processor basis. Instead, a plurality of independent circuits may be combined to be configured as one processor, and may perform the functions thereof. Furthermore, a plurality of components in the figures may be integrated into one processor, and may perform the functions thereof.

The configuration example of the ultrasonic diagnostic apparatus 1 according to the first embodiment has been described above. Under such a configuration, the ultrasonic diagnostic apparatus 1 according to the first embodiment performs the following processing to analyze a region of the subject P for each area of the region divided based on positions representing anatomical features.

The following describes a case where the processing circuitry 170 uses a three-dimensional speckle tracking (3DT) method to analyze cardiac wall motion. The embodiments are, however, not limited to this case. The processing circuitry 170 is not limited to analyzing the cardiac wall motion, but can, for example, calculate volume information on the volume of the heart. The processing circuitry 170 is not limited to analyzing the heart, but can analyze other regions (organs).

The acquiring function 171 acquires the three-dimensional medical image data obtained by imaging a region of the subject P. The acquiring function 171 acquires, for example, the three-dimensional medical image data obtained by imaging the heart of the subject P for at least one heartbeat. The acquiring function 171 is an example of an acquiring unit. In other words, the acquiring function 171 acquires time-series volume data obtained by imaging a region of the subject in motion.

For example, the operator uses a sector probe to perform the three-dimensional scanning of an area including the heart of the subject P, and thus captures moving image data of the three-dimensional ultrasonic image data representing a cardiac muscle. This moving image data is, for example, an ultrasonic image data group including ultrasonic image data collected using a B-mode technique on a time phase-by-time phase basis. The term "time phase" refers to any time point (timing) during the periodic motion of the heart, and is also called "cardiac phase".

The image generation circuitry 140 generates the moving image data of the right ventricle of the heart, and stores the generated moving image data in the image memory 150. The operator sets, for example, an interval of one heartbeat from an R wave to the next R wave in an electrocardiogram as an interval to be processed. The present embodiment can be applied to a case where the interval to be processed is set to be an interval of two heartbeats or three heartbeats.

The acquiring function 171 acquires, for example, the ultrasonic image data group from the image memory 150. This ultrasonic image data group includes a plurality of frames of the three-dimensional ultrasonic image data (volume data) included in the interval of one heartbeat that has been set by the operator.

In the first embodiment, to describe a typical application example to the speckle tracking method, the case has been described where the volume data across a plurality of time phases is acquired. The embodiments are, however, not limited to this case. The acquiring function 171 may acquire, for example, the volume data corresponding to one time phase. Accordingly, the acquiring function 171 may acquire, for example, the volume data of one time phase corresponding to an end-systole or an end-diastole.

In the first embodiment, a case will be described where the acquiring function 171 acquires the three-dimensional ultrasonic image data obtained by imaging the right ventricle, and uses the acquired the three-dimensional ultrasonic image data for the following processing. The embodiments are, however, not limited to this case. For example, the three-dimensional ultrasonic image data acquired by the acquiring function 171 may have been obtained by imaging the left ventricle, or may have been obtained by imaging the entire heart or a region other than the heart.

In the first embodiment, a case will be described where the three-dimensional ultrasonic image data generated by the transmission and reception of the ultrasound is used as the three-dimensional medical image data. The embodiments are, however, not limited to this case. The three-dimensional medical image data may be, for example, three-dimensional medical image data generated by a medical image diagnostic apparatus other than the ultrasonic diagnostic apparatus.

The identification information setting function 172 sets identification information for identifying each of a plurality of positions representing a contour of a region of the subject P, in the three-dimensional medical image data. The identification information setting function 172 is an example of an identification information setting unit.

For example, the identification information setting function 172 sets a plurality of track points (constituting points) assigned with address numbers to positions corresponding to the contour of the right ventricle in at least one piece of the ultrasonic image data included in the ultrasonic image data group. The track points are points that are tracked over time to calculate the motion information in a local area, and are constituting points constituting the contour of the local area. The address numbers are numbers assigned to identify the respective track points, and are defined, for example, based on the positions of the respective track points of the endocardium of the heart. The address numbers are not limited to numbers (digits), but only need to be identification information, such as characters or symbols, that can identify the positions of the respective track points.

As an example, a case will be described where the following processing is applied to the endocardium of the right ventricle. The embodiments are, however, not limited to this case. For example, the following processing is not limited to being applied to the endocardium, but may be applied to the epicardium or an intermediate layer between the endocardium and epicardium. The identification information setting function 172 is not limited to applying the following processing to the right ventricle, but may apply the following processing to any given area, such as the left ventricle, the left atrium, the right atrium, or the entire heart. In the present embodiment, the identification information setting function 172 uses information manually set by the operator to set the constituting points constituting the contour in positions corresponding to an initial contour of the right ventricle.

For example, the operator specifies any cardiac phase for the ultrasonic image data group acquired by the acquiring function 171. The cardiac chase thus specified corresponds to any one of frames included in the interval of one heartbeat, and is, for example, the end-diastole time phase (first R wave time phase). After the operator specifies the cardiac phase, the identification information setting function 172 sets a three-dimensional initial contour for the ultrasonic image data at the specified cardiac phase.

The three-dimensional initial contour is generated, for example, by applying interpolation processing to two-dimensional contour lines entered for a plurality of reference MPR cross-sections. For example, the operator enters contour lines representing the contour of the endocardium of the right ventricle for the respective reference MPR cross-sections passing through the apical part. The identification information setting function 172 converts positions of the contour lines entered in the respective reference MPR cross-sections into coordinates of the three-dimensional ultrasonic image data. The identification information setting function 172 performs the spatial interpolation processing between the contour lines to generate the three-dimensional contour shape (initial contour) between the respective contour lines in the three-dimensional ultrasonic image data. In this manner, the identification information setting function 172 sets the initial contour of the endocardium of the right ventricle.

Figure 2:
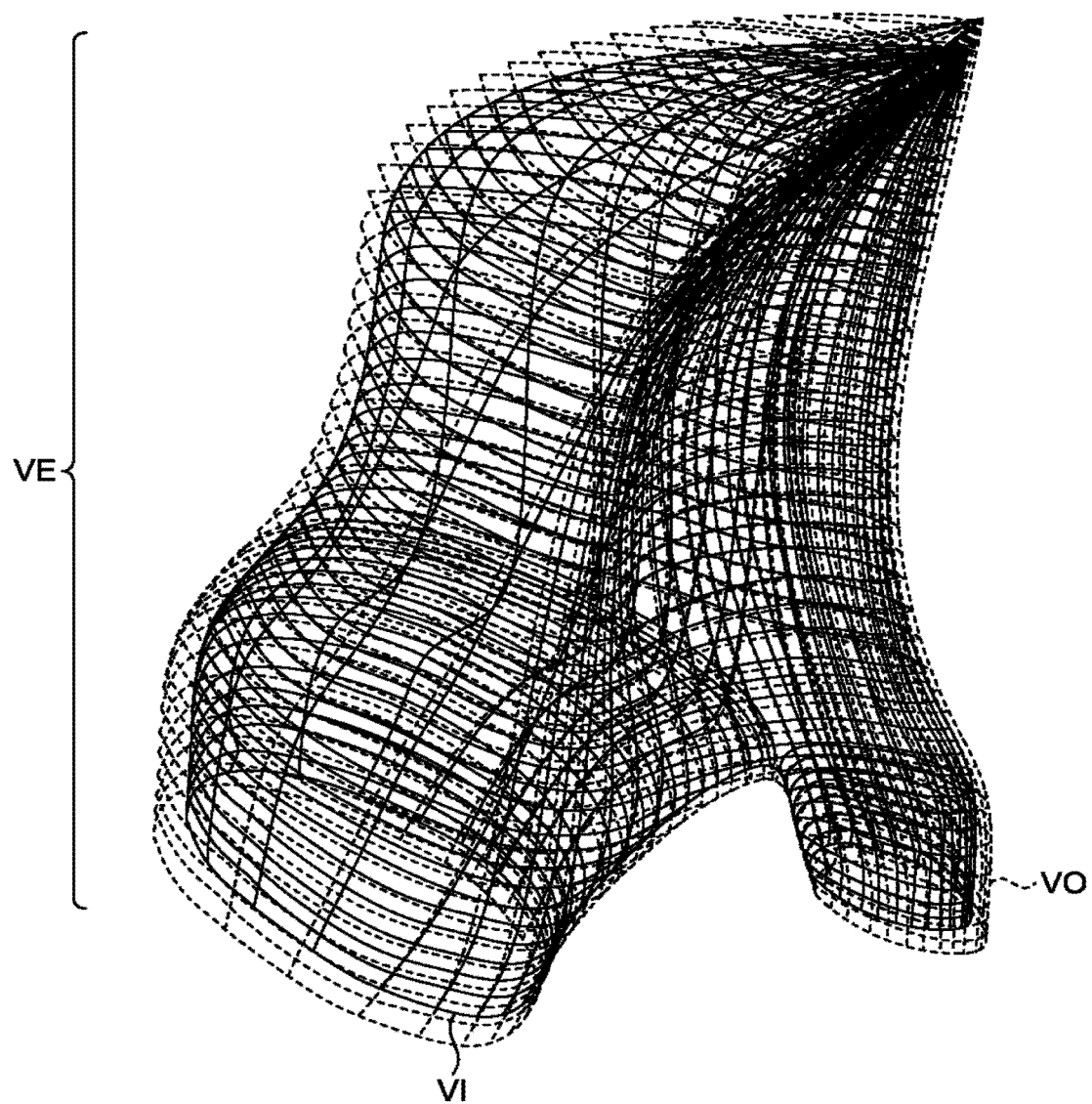
FIG. 2 is a diagram for explaining initial contours set by an identification information setting function according to the first embodiment.

FIG. 2 is a diagram for explaining initial contours set by the identification information setting function 172 according to the first embodiment. FIG. 2 illustrates initial contours (VE) set on the right ventricle. In FIG. 2, a mesh-like structure represented by solid lines corresponds to an initial contour set on the endocardium of the right ventricle, and a mesh-like structure represented by dashed lines corresponds to an initial contour set on the epicardium of the right ventricle. FIG. 2 illustrates an inflow port (VI) through which the blood flows into the right ventricle and an outflow port (VO) through which the blood flows out thereof.

As illustrated in FIG. 2, the identification information setting function 172 sets the three-dimensional initial contour (VE), among pieces of the ultrasonic image data at any cardiac phase, in a position corresponding to the endocardium of the right ventricle. The identification information setting function 172 assigns address numbers to a plurality of constituting points constituting the initial contour (VE) thus set. In the example illustrated in FIG. 2, the constituting points correspond to intersections of the mesh-like structure. The identification information setting function 172 assigns the address numbers to the constituting points set in the positions of the intersection of the mesh-like structure.

For example, the identification information setting function 172 defines the position of each of the constituting points of the endocardium of the heart as P_endo(t,h,d), where t denotes the frame (cardiac phase) included in the interval of one heartbeat, h denotes the address number in the long axis direction (height), and d denotes the address number in the circumferential direction (orientation). In this case, t=0, because the first R wave time phase is used to set the initial cross-section.

The identification information setting function 172 sets a reference position in the circumferential direction, for example, at an end on the tricuspid valve side of the right ventricle, and sets d of the constituting point in the reference position to 0. In other words, the position of the constituting point in this reference position is represented as P_endo(0, h,0). The identification information setting function 172 sequentially assigns the address numbers d=0, 1, 2, 3, . . . to the constituting points arranged in the circumferential direction starting from the constituting point in the reference position. The identification information setting function 172 sets a reference position in the long axis direction at the location of an annular contour portion of the three-dimensional initial contour located farthest from the apical part, and sets h of the constituting point in the reference position to 0. In other words, the position of the constituting point in this reference position is represented as P_endo(0,0,d). The identification information setting function 172 sequentially assigns the address numbers h=0, 1, 2, 3, . . . to the constituting points arranged in the apical direction starting from the constituting point in the reference position.

In this manner, the identification information setting function 172 sets the track points constituting points) assigned with the address numbers in the positions corresponding to the endocardium of the right ventricle in the three-dimensional medical image data. The initial contour is not limited to being set by the manual operation described above. The identification information setting function 172 may automatically or semi-automatically detect boundaries in the image using dictionary data of contour shapes of the endocardium (such as statistical data of previously set contours).

The ROI setting function 173 sets an ROI in the three-dimensional medical image data. For example, the ROI setting function 173 sets the ROI in an area corresponding to the right ventricle of the heart included in the three-dimensional medical image data. Specifically, the ROI setting function 173 sets the ROI in the area corresponding to the right ventricle based on a way of boundary detection for the right ventricle or a manual way of setting the boundary position (such extraction of the boundary position is called segmentation, in general). The ROI setting function 173 is an example of an ROI setting unit.

Figure 3A:
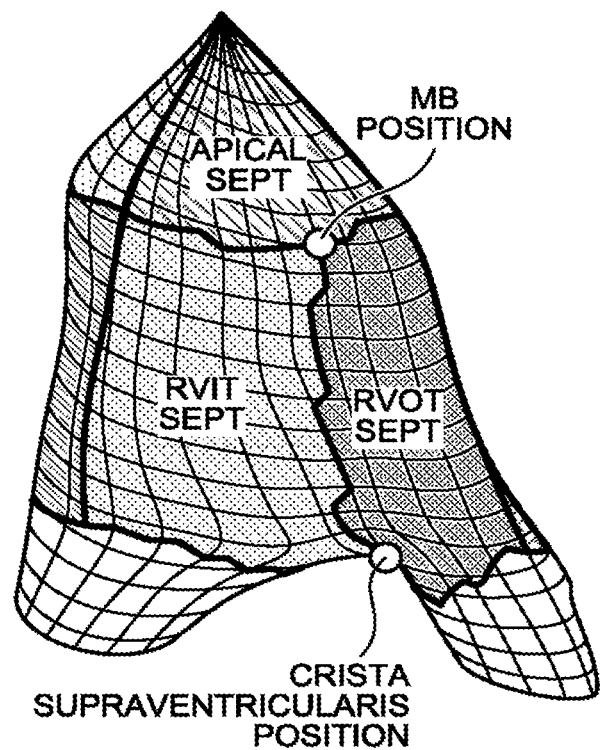
FIGS. 3A to 3C are diagrams for explaining processing of a region-of-interest (ROI) setting function according to the first embodiment.
Figure 3B:
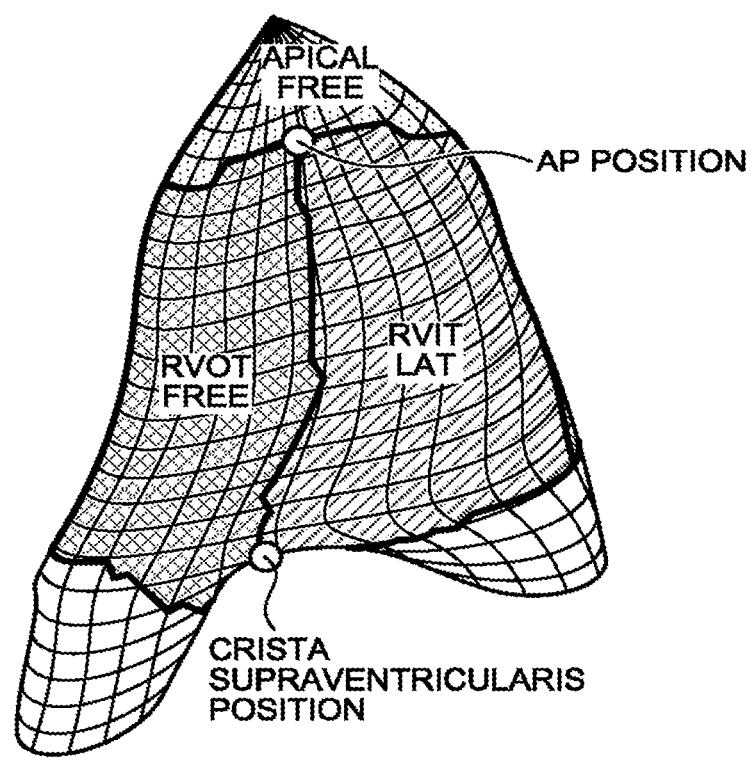
Figure 3C:
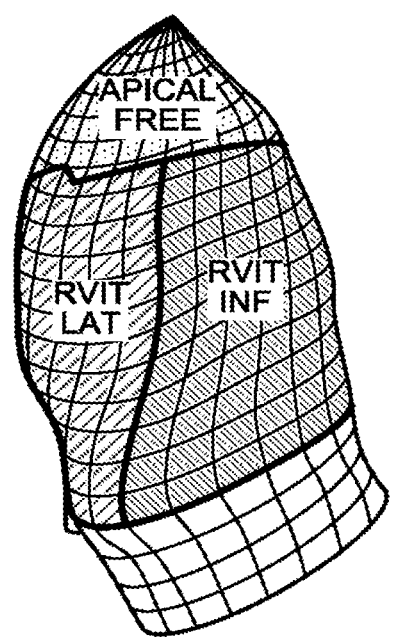

FIGS. 3A to 3S are diagrams for explaining the processing of the ROI setting function 173 according to the first embodiment. FIGS. 3A to 3S illustrate the ROI set by the ROI setting function 173. FIG. 3A is a diagram obtained by viewing the right ventricle from the interventricular septum (IVS) side thereof. FIGS. 3B and 3C are diagrams obtained by viewing the right ventricle from the free wall side thereof.

As illustrated in FIGS. 3A to 3C, the ROI setting function 173 sets the ROI in the area corresponding to the right ventricle of the heart included in the ultrasonic image data. This ROI is divided into the following seven segments (divided regions): an interventricular septum side inflow part (RVIT Sept), an interventricular septum side outflow part (RVOT Sept), an interventricular septum side apical part (Apical Sept), a free wall side outflow part (RVOT Free), a free wall side apical part (Apical Free), a lateral wall side inflow part (RVIT Lat), and an inferior wall side inflow part (RVIT Inf).

The dividing positions of the ROI set by the ROI setting function 173 are associated with biological landmark positions (feature positions) that represent the anatomical features in the living body. Taking the right ventricle as an example, according to the structure of the right ventricular lumen, which are also called a right ventricular ring (hereinafter, also referred to as "RV ring"), the right ventricle is anatomically divided into the following two regions: a region on the inflow port side (hereinafter, also referred to as "inflow part") and a region on the outflow port side (hereinafter, also referred to as "outflow part"). Hence, the dividing positions of the ROI set at the right ventricle can be anatomically meaningful positions by being associated with the biological landmark positions on the RV ring.

Figure 4A:
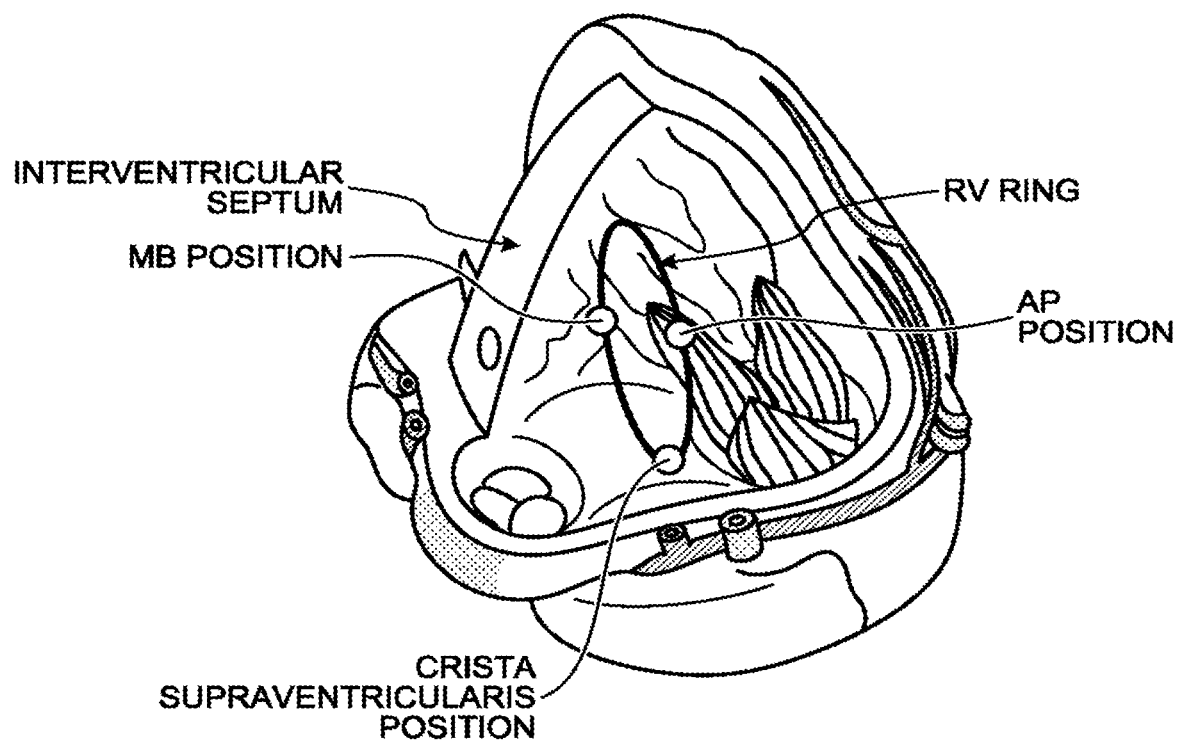
FIGS. 4A and 4B are diagrams for explaining a position of a right ventricular (RV) ring.
Figure 4B:
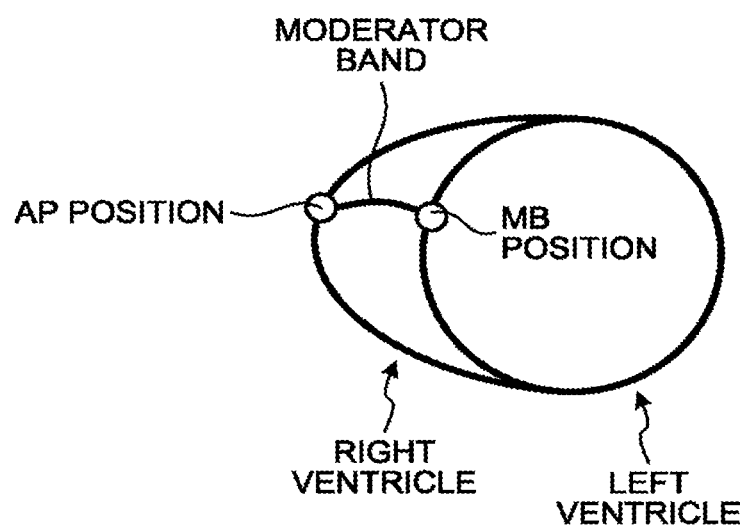

FIGS. 4A and 4B are diagrams for explaining the position of the RV ring. FIG. 4A illustrates an anatomical model diagram that illustrates a state of the right ventricular lumen by developing the free wall of the right ventricle. FIG. 4A illustrates the interventricular septum on the far side, the inflow port on the right side, and the outflow port on the left side. FIG. 4B illustrates a schematic diagram of a cross-section (corresponding to a short-axis section of the ventricle, in this example) passing through two of the landmark positions on the RV ring. FIG. 4B illustrates the right ventricle on the left side and the left ventricle on the right side.

The RV ring lies in the position indicated by the RV ring in FIG. 4A. Three main biological landmarks define the position of the right ventricular ring, as illustrated in FIGS. 4A and 4B. These regions correspond to the crista supraventricularis (termed "crista supraventricularis position" in FIG. 4A) serving as an apex of the endocardial wall between the inflow port and the outlet port, to the anterior papillary muscle (termed "AP position" in FIGS. 4A and 4B) on the free wall side of the right ventricle, and to a region (termed "MB position" in FIGS. 4A and 4B) where the trabecula septomarginalis on the interventricular septum side of the right ventricle shifts to the moderator band. (For the RV ring, refer to Osamu Igawa, "Practice and Anatomical Knowledge of Alternative Pacing", Proceedings of 34th Symposium of Saitama Society of Facing and Electrophysiology, Page 13, Column 1, Line 28 to Page 33, Column 1, Line 14.)

These biological landmarks are distinctive structural objects among the muscle fascicles forming the RV ring. In particular, the MB position and the AP position are represented as relatively highly luminous structural objects projecting in the right ventricular chamber, in the ultrasonic image data. The crista supraventricularis position is easily identified as a top position of the bottom surface connecting together the inflow part and the outflow part of the three-dimensional medical image data.

Hence, in the first embodiment, the dividing positions of the ROI set by the ROI setting function 173 are associated with the biological landmark positions (feature positions) that represent the anatomical features in the living body. Specifically, the MB position corresponds to a position where the ROI is divided into three segments of the interventricular septum side inflow part (RVIT Sept), the interventricular septum side outflow part (RVOT Sept), and the interventricular septum side apical part (Apical Sept) (refer to FIG. 3A). Also, the AN position corresponds to a position where the ROI is divided into three segments of the free wall side outflow part (RVOT Free), the lateral wall side inflow part (RVIT Lat), and the free wall side apical part (Apical Free) (refer to FIG. 3B).

In this manner, the ROI setting function 173 sets the ROI in which the dividing positions are defined by the biological landmark positions, in the three-dimensional medical image data. Specifically, the ROI setting function 173 sets, in the three-dimensional medical image data, the ROI that is divided into a plurality of divided regions and in which a feature position representing an anatomical feature of a region is associated in advance with at least one of the dividing positions between the divided regions. In other words, the ROI setting function 173 sets at least one feature position that represents an anatomical feature in the ROI. The biological landmark positions in the ROI have been preset, for example, based on the statistical data of previously set contours, and when the ROI setting function 173 sets the ROI, the biological landmark positions in the ROI are initially set in statistically likely positions. The biological landmark positions in the ROI are adjustable by processing to be described later.

The calculating function 174 calculates, from the three-dimensional medical image data, at least either of the volume information representing the volume of the ROI and the motion information representing the motion function of the ROI. For example, the calculating function 174 performs a tracking process including pattern matching using the ultrasonic image data at an initial time phase in which a plurality of constituting points are set and the ultrasonic image data at the next time phase, and thus tracks the positions of the constituting points in a plurality of pieces of the ultrasonic image data included in the ultrasonic image data group. The calculating function 174 is an example of a calculating unit. In other words, the calculating function 174 uses the volume data to calculate at least either of the volume information and the motion information on the ROI by performing processing including the tracking.

For example, after the constituting points are set in positions corresponding to the initial contour in the volume data of the frame at t=0 included in the volume data group, the calculating function 174 performs the processing including the pattern matching to track the positions of the constituting points in another frame t. Specifically, the calculating function 174 repeats the pattern matching between the volume data of a frame in which the constituting points are already set and a frame adjacent to the frame. In other words, the calculating function 174 begins at the constituting point in P_endo(0,h,d) on the endocardium of the heart in the volume data at t=0, and tracks the position of each of the constituting points in P_endo(t,h,d) in the volume data of each frame at t=1, 2, 3, . . . . As a result, the calculating function 174 obtains coordinate information on the constituting points constituting the endocardium of the heart.

The calculating function 174 uses the positions of the constituting points in the nieces of the ultrasonic image data included in each ultrasonic image data group to calculate the motion information representing the motion of the tissue for each of the pieces of the ultrasonic image data.

Typical examples of the motion information calculated by the calculating function 174 include, but are not limited to, a local myocardial displacement (mm) for each frame of each constituting point, a local myocardial strain (%) serving as a ratio of change in distance between two points, and a local myocardial velocity (cm/s) and a local myocardial strain rate (1/s) serving as temporal changes in the amounts mentioned above. The motion information is, however, not limited to these parameters, but only needs to be parameters that can be calculated using the coordinate information on the constituting points in each of the frames. For example, these pieces of motion information may be separated into components. In the case of the right ventricle, for example, a longitudinal strain (LS) separated as a component in the long axis (longitudinal) direction and a circumferential strain (CS) separated as a component in the circumferential direction are used as indicators. These indicators are calculated by a two-dimensional speckle tracking method using a two-dimensional image (a long axis image or a short-axis image) of the right ventricle. If a three-dimensional speckle tracking method is used, a local area change (AC) ratio may be defined. The AC need not be separated into a directional component. Hence, a complicated shape, such as that of the right ventricle, can be analyzed in a stable manner.

Examples of the motion information often clinically used for functional evaluation of the right ventricle include, but are not limited to, tricuspid annular plane systolic excursion (TAPSE) that is measured using an M-mode technique. Since the M-mode technique is a one-dimensional analysis, measuring the TAPSE allows observation of a displacement component of a part near the tricuspid annulus in a direction toward the ultrasonic probe for a part near the tricuspid annulus. In contrast, using the three-dimensional speckle tracking method allows acquisition of information on the displacement covering the entire area of the right ventricle. In this case, the displacement components can be detected in the long axis direction and the wall thickness (radial) direction with respect to the ROI (right ventricle). A moving distance D (D=sqrt((Px(n)−Px(n0))^2+(Py(n)−Py(n0))^2+(Pz(n)−Pz(n0))^2)) that is not separated into directional components may be used as an indicator hardly influenced by the complicated shape of the right ventricle. The notation (Px(n),Py(n),Pz(n)) denotes the position of a track point P, n denotes the time phase, and n0 denotes a reference time phase.

The motion information calculated by the calculating function 174 is assigned to the constituting points (track points) used for the calculation. Specifically, for example, the motion information calculated from the constituting points of the endocardium of the right ventricle is defined as V_endo(t,h,d). The calculating function 174 stores the calculated motion information, volume data group by volume data group, in the image memory 150.

The calculating function 174 calculates the volume information as an indicator of a pumping function of the heart. The calculating function 174 calculates the volume information on, for example, the ROI including the right ventricle. The region on which the volume information is calculated by the calculating function 174 can be changed as appropriate.

In this manner, the calculating function 174 calculates the information including at least either of the volume information and the motion information on the heart, regarding the ultrasonic image data group.

The two-dimensional image generating function 175 generates, from the three-dimensional medical image data, cross-sectional image data of a cross-section passing through a feature position representing an anatomical feature of region. For example, the two-dimensional image generating function 175 generates, from the ultrasonic image data, cross-sectional image data passing through a biological landmark position. Specifically, the two-dimensional image generating function 175 generates (reconstructs), from the ultrasonic image data at any time phase included in the ultrasonic image data group, the MPR image data that passes through two points of the MB and AP positions serving as the dividing positions of the ROI. The two-dimensional image generating function 175 is an example of a two-dimensional image generating unit. The two-dimensional image generating unit is an example of an image generating unit.

For example, the two-dimensional image generating function 175 generates the MPR image data that passes through a total of three points including any segment boundary point in addition to the two points of the MB and AP positions. The segment boundary point corresponds to, for example, a boundary point in a position where the ROI is divided into the segments of the free wall side apical part (Apical Free), the lateral wall side inflow part (RVIT Lat), and the inferior wall side inflow part (RVIT Inf). This segment boundary point spaced by large distances from the two points of the MB and AP positions. Hence, the two-dimensional image generating function 175 can generate the MPR image data that has an inclination approximate to that of the short-axis section of the right ventricle (C plane in an apical approach).

Figure 5:
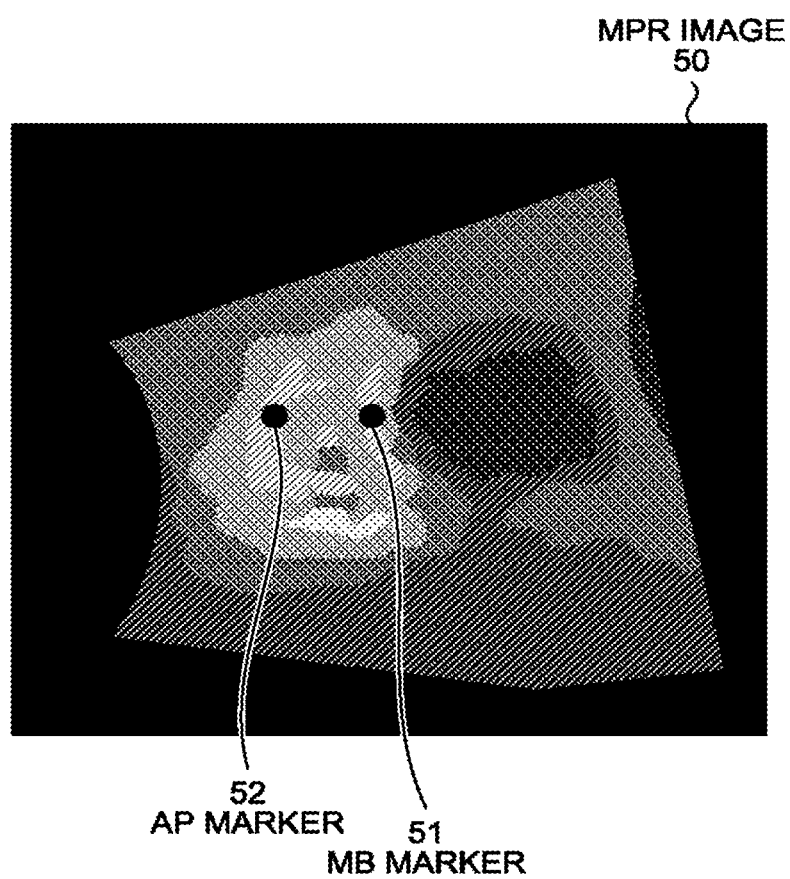
FIG. 5 is a view for explaining processing of a two-dimensional image generating function according to the first embodiment.

FIG. 5 is a view for explaining the processing of the two-dimensional image generating function 175 according to the first embodiment. FIG. 5 illustrates an MPR image 50 generated by the two-dimensional image generating function 175.

As illustrated in FIG. 5, the two-dimensional image generating function 175 generates the MPR image 50 having an inclination approximate to that of the short-axis section. The MPR image 50 passes through the two points of the MB and AP positions, and consequently can represent the MB position and the AP position. Hence, the two-dimensional image generating function 175 generates an MB marker 51 indicating the MB position and an AP marker 52 indicating the AP position.

In this manner, the two-dimensional image generating function 175 generates the MPH image data that passes through at least the two points of the MB and AP positions. The MPR image data generated by the two-dimensional image generating function 175 is displayed on the display 103 by the output controlling function 176 to be described later. In other words, the two-dimensional image generating function 175 serving as the image generating unit generates the MPR image that passes through at least one feature position.

The output controlling function 176 displays a display image based on the cross-sectional image data, and outputs at least either of the volume information and the motion information corresponding to the divided regions obtained by dividing the ROI based on the feature positions. For example, the output controlling function 176 outputs at least either of the volume information and the motion information on each of the divided regions obtained by dividing the ROI with boundary lines passing through the feature positions. The output controlling function 176 also outputs at least either of the volume information and the motion information on each of a plurality of divided regions obtained by further dividing the ROI with boundary lines not passing through the feature positions. The output controlling function 176 is an example of an output controlling unit. In other words, the output controlling function 176 displays the MPR image, and outputs at least either of the information that includes the feature positions as boundaries.

Figure 6:
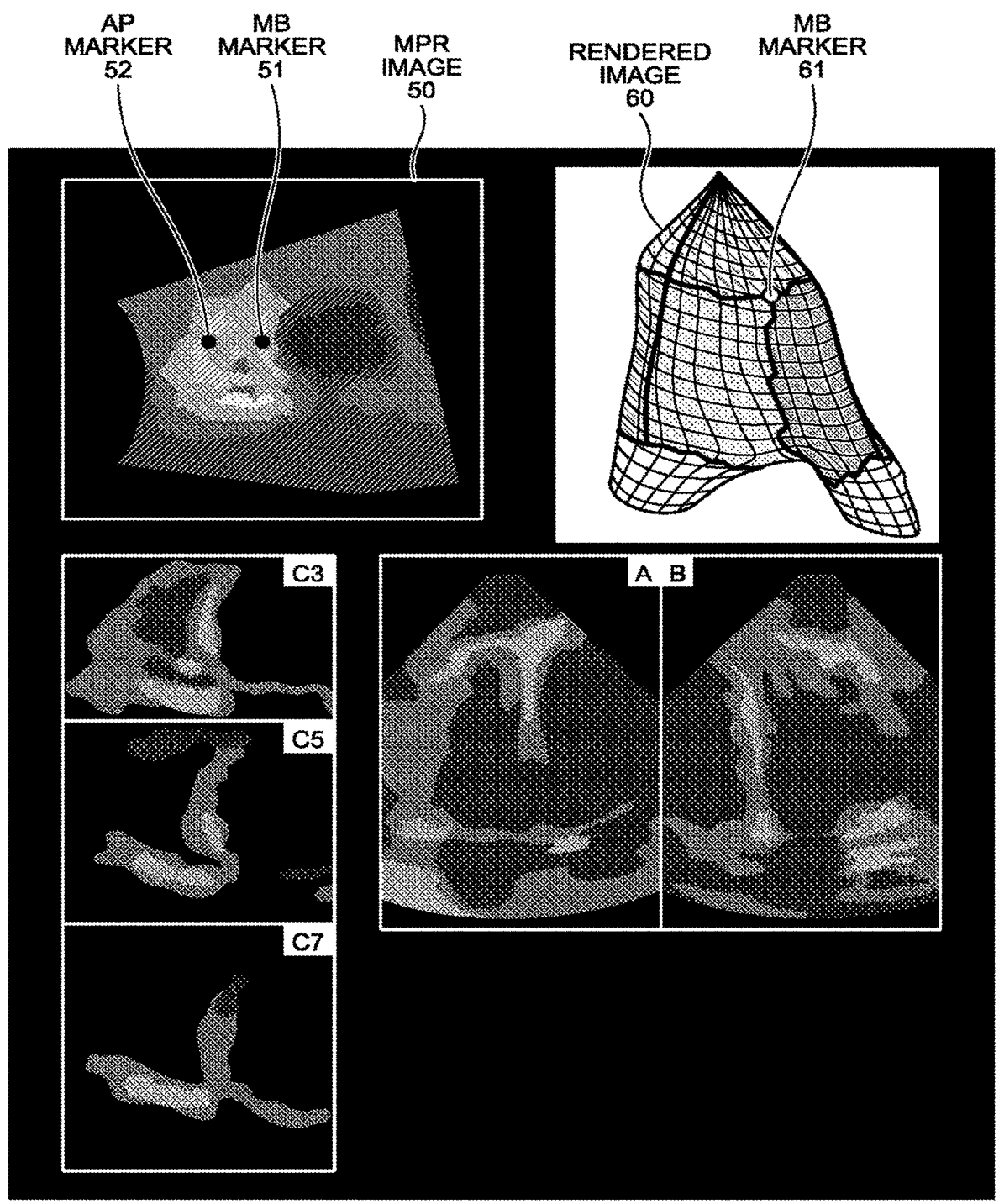
FIG. 6 is a view illustrating an example of a display screen displayed by an output controlling function according to the first embodiment.

FIG. 6 is a view illustrating an example of a display screen displayed by the output controlling function 176 according to the first embodiment. FIG. 6 illustrates, on the upper left side thereof, the MPR image 50 based on the cross-sectional image data. FIG. 6 illustrates, on the upper right side thereof, a rendered image 60 generated by the rendering processing of the ultrasonic image data. FIG. 6 illustrates, on the lower side thereof, cross-sectional images in the A plane, the B plane, and the C plane of levels 3 to 7. The A and B planes represent MPR images in the long axis direction, the A plane representing an apical four-chamber view and the B plane representing a right ventricular coronal view substantially orthogonal to the A plane at the inflow part of the right ventricle. The C plane is a short-axis section substantially orthogonal to the long axis direction, and, in this example, internally has nine levels, of which C2, C5, and C7 represent MPR images corresponding to respective ones of the levels.

As illustrated on the upper left side of FIG. 6, the output controlling function 176 generates the MPR image 50 for display based on the cross-sectional image data generated by the two-dimensional image generating function 175. The output controlling function 176 displays the MB marker 51 indicating the MB position and the AP marker 52 indicating the AP position in a superimposed manner on the MPR image 50. This display allows the operator to determine, by viewing the MPR image 50, whether the MPR image correctly passes through the two points of the MB and AP positions. For example, since the MB and AP positions are represented at high luminance in the ultrasonic image, the operator can determine whether the MPR image correctly passes through the two points of the MB and AP positions by checking the luminance of positions around the MB marker 51 and the AP marker 52. In addition, in this MPR cross-section, the moderator band with the MB and AP positions located at both ends thereof is visible in the right ventricular chamber in some cases. This fact is useful for determining the validity of the MB and AP positions. The MB marker 51 and the AP marker 52 are examples of first markers.

The output controlling function 176 applies surface rendering processing to the ROI at a cardiac phase corresponding to the MPR image 50 to generate the rendered image 60, and displays it on the display 103, as illustrated on the upper right side of FIG. 6. The output controlling function 176 displays an MB marker 61 indicating the MB position on the septal wall side in a superimposed manner on the rendered image 60. This display allows the operator to three-dimensionally understand the MB position in the rendered image 60 by viewing the rendered image 60. Although not illustrated, an AP marker 62 indicating the AP position on the free wall side is located on the backside of the rendered image 60 generated by the surface rendering processing. The operator can also three-dimensionally understand the AP position in the same manner as the MB position by revolving the viewing position of the rendered image 60 to display the backside, and observing the state on the free wall side. The MB marker 61 is an example of a second marker.

The output controlling function 176 preferably converts the local wall motion information calculated by the calculating function 174 into color codes and maps the results on the rendered image 60. Alternatively, the output controlling function 176 calculates, for each of the seven segments included on the ROI, the average value of the regional wall motion information defined at the address of each vertex in the ROI calculated by the calculating function 174. The output controlling function 176 creates and displays a time variation curve of the calculated average value. In this manner, the output controlling function 176 can provide the functional analysis of the right ventricle on a segment-by-segment basis.

For convenience of illustration, FIG. 6 illustrates the MB marker 51 and the AP marker 52 with black circles. However, the MB marker 51 and the AP marker 52 are actually preferably displayed in a manner distinguished from each other by different colors (or different shapes). For example, the MB marker 51 is displayed in pink, and the AP marker 52 is displayed in cyan. This approach allows the operator to easily distinguish between the MB position and the AP position in the MPR image 50.

The display colors of the MB marker 61 and the AP marker 62 in the rendered image 60 are preferably the same as the display colors of the MB marker 51 and the AP marker 52, respectively, in the MPR image. This approach allows the operator to easily understand the correspondence of the MB and AP positions between the MPR image 50 and the rendered image 60.

In the first embodiment, the case has been described where the MPR image 50 having an inclination approximate to that of the short-axis section is generated. The embodiments are, however, not limited to this case. For example, the two-dimensional image generating function 175 may generate curved-MPR image data having a curved surface passing through three points, instead of the above-described cross-section passing through the three points. In this case, a MPR image corresponding to segment boundary positions at apical levels is obtained.

Alternatively, the two-dimensional image generating function 175 may generate, for example, MPR image data that passes through three points of the crista supraventricularis position serving as a fixed point, the MB position, and the AP position. In this case, the displayed MPR image can represent the RV ring. The two-dimensional image generating function 175 may generate the curved-MPR image data having a curved surface passing through the three points of the MB position, the AP position, and the crista supraventricularis position. In this case, a plane dividing the inflow part from the outflow part of the right ventricle can be clearly represented. When the ROI of the right ventricle is divided in this MPR position, the volume of each of the inflow part and the outflow part can be analyzed individually. The crista supraventricularis position can be calculated as an apex position (position nearest to the apical part) of the contour on the base side of the right ventricle. This MPR plane always passes through the crista supraventricularis. However, the highly luminous oval lumen at the outflow part appears to be cut when viewed on the MPH plane having any angle from the fixed point. As a result, it is difficult in some cases to determine, based on the MPR display, whether the MPH plane actually includes two biological landmarks of the MB position and the anterior papillary muscle.

Hence, for example, the two-dimensional image generating function 175 displays both the MPR image passing through the two points of the MB and AP positions according to the first embodiment and the MPR image passing through the above-described crista supraventricularis serving as a fixed point. In this case, the two points of the MB and AP positions in the latter of the above-mentioned MPR images correspond to the respective positions in the former of the above-mentioned MPR images. An MPR image passing through the three biological landmark positions defining the position of the right ventricular ring can be easily obtained by using the MPR display of the latter of the above-mentioned MPR images after correctly determining the positions of the two points of the MB and AP positions using the MPR display of the former of the above-mentioned MPR images.

As will be described later, the adjusting function 177 adjusts (moves) the MB and AP positions. In this case, each time the MB and AP positions serving as biological landmark positions have been adjusted, the two-dimensional image generating function 175 uses the biological landmark positions after being adjusted to generate the cross-sectional image data. Each time the two-dimensional image generating function 175 has generated the cross-sectional image data, the output controlling function 176 displays the display image based on the generated cross-sectional image data.

The adjusting function 177 receives an operation performed by the operator, and adjusts, according to the operation thus received, a feature position to a position on which the identification information has been set. For example, the adjusting function 177 receives, from the operator, an operation specifying the direction and distance of moving the feature position in a rendered image based on the three-dimensional medical image data, and adjusts the feature position according to the direction and the distance. The adjusting function 177 is an example of an adjusting unit.

Figure 7A:
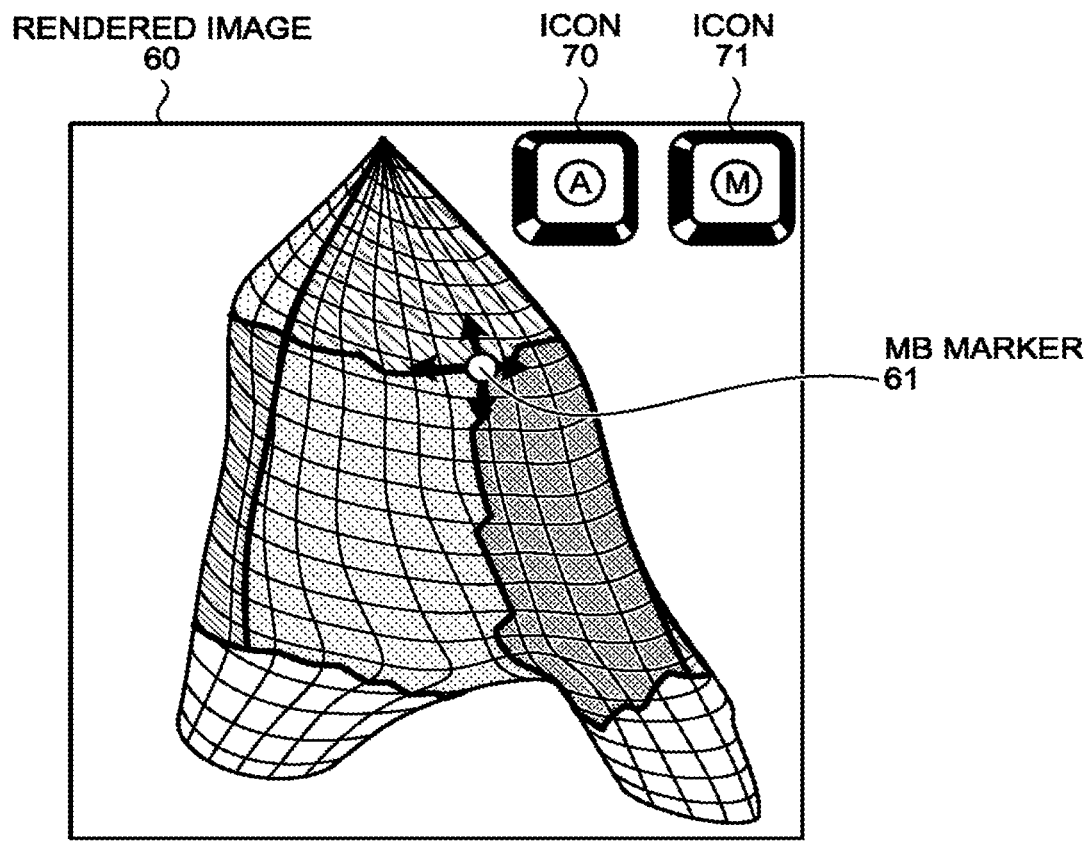
FIGS. 7A and 7B are diagrams for explaining processing of an adjusting function according to the first embodiment.
Figure 7B:
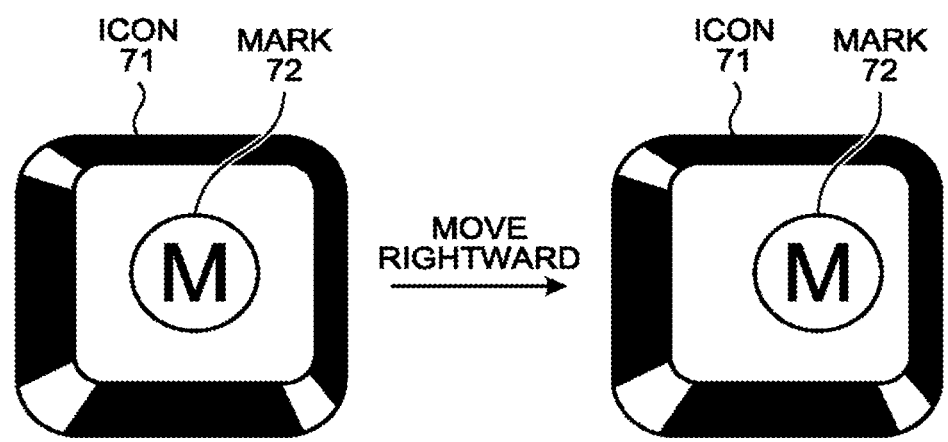

FIGS. 7A and 7B are diagrams for explaining the processing of the adjusting function 177 according to the first embodiment. FIG. 7A illustrates the rendered image 60 displayed on the display 103 by the output controlling function 176. An icon 70 and an icon 71 are displayed as keyboard-like graphical user interface (GUI) elements for position adjustment in the rendered image 60. The icon 70 is a key-shaped GUI element for adjusting the AP position, and is marked with "A". The icon 71 is a key-shaped GUI element for adjusting the MB position, and is marked with "M". FIG. 7B illustrates a state of adjusting the MB position using the icon 71. The following describes, with reference to FIGS. 7A and 7B, a case of adjusting the MB position by moving the position of the MB marker 61 in the rendered image 60. The same processing applies to a case of adjusting the AP positron. In the description with reference to FIGS. 7A and 7B, the position (address number) of the MB marker 61 before being adjusted is (t0,h0,d0).

As illustrated in FIG. 7A, the adjusting function 177 displays the icon 70 for adjusting the AP position and the icon 71 for adjusting the MB position, in the rendered image 60. To adjust the MB position, the operator performs an operation of selecting the icon 71. After receiving from the operator the operation of selecting the icon 71, the adjusting function 177 set the MB position as a position to be adjusted. The adjusting function 177 displays movable directions of the MB marker 61 in the rendered image 60. In the example illustrated in FIG. 7A, the adjusting function 177 displays, around the MB marker 61, an upward arrow, a downward arrow, a rightward arrow, and a leftward arrow, as movable directions of the MB marker 61.

As illustrated in FIG. 7B, the adjusting function 177 adjusts, according to an operation to a mark 72 performed by the operator, the position of the MB marker 61 to a position (constituting point) assigned with an address. In the example illustrated in FIG. 7B, a case will be described where the operator performs a drag operation to move the mark 72 of "M" rightward. In this case, the adjusting function 177 moves the MB marker 61 rightward according to the rightward movement of the mark 72. Specifically, the adjusting function 177 changes the address number of the MB marker 61 according to the moving direction and the moving distance of the mark 72. For example, if the rightward movement of the mark 72 corresponds to the "positive direction" in the circumferential direction and the moving distance corresponds to "3", the adjusting function 177 adds "+3" to the position in the circumferential direction of the MB marker 61. As a result, the adjusting function 177 changes the position of the MB marker 61 from (t0,h0,d0) to (t0,h0,d0+3).

In this manner, the adjusting function 177 adjusts, according to the operation performed by the operator, the biological landmark position to the position assigned with the address number. After the biological landmark position is adjusted, the two-dimensional image generating function 175 uses the biological landmark position after being adjusted to generate the cross-sectional image data. Each time the two-dimensional image generating function 175 has updated the cross-sectional image data, the output controlling function 176 displays the display image based on the generated cross-sectional image data.

The processing to adjust the biological landmark position is not limited to the description above. For example, in the description above, the case has been described where the moving direction of the mark 72 agrees with that of the MB marker 61. The moving direction is, however, not limited to this case. For example, the moving directions of the mark 72 and the MB marker 61 need not agree with each other if the moving directions of both these elements correspond to each other.

The configuration for receiving the operation of specifying the direction and distance of movement of the biological landmark position from the operator is not limited to the configuration illustrated in FIGS. 7A and 7B. For example, the operation of specifying the direction and distance of movement may be received through keyboard operations. For example, when the operator presses the "right" key of the arrow keys three times while keeping pressing the "M" key of the keyboard, the adjusting function 177 may receive this operation as an operation to move the MB marker 61 by "+3" in the circumferential direction; or when the operator presses an arrow key while keeping pressing the "A" key of the keyboard, the adjusting function 177 may receive this operation as an operation to move the AP marker 62.

Figure 8:
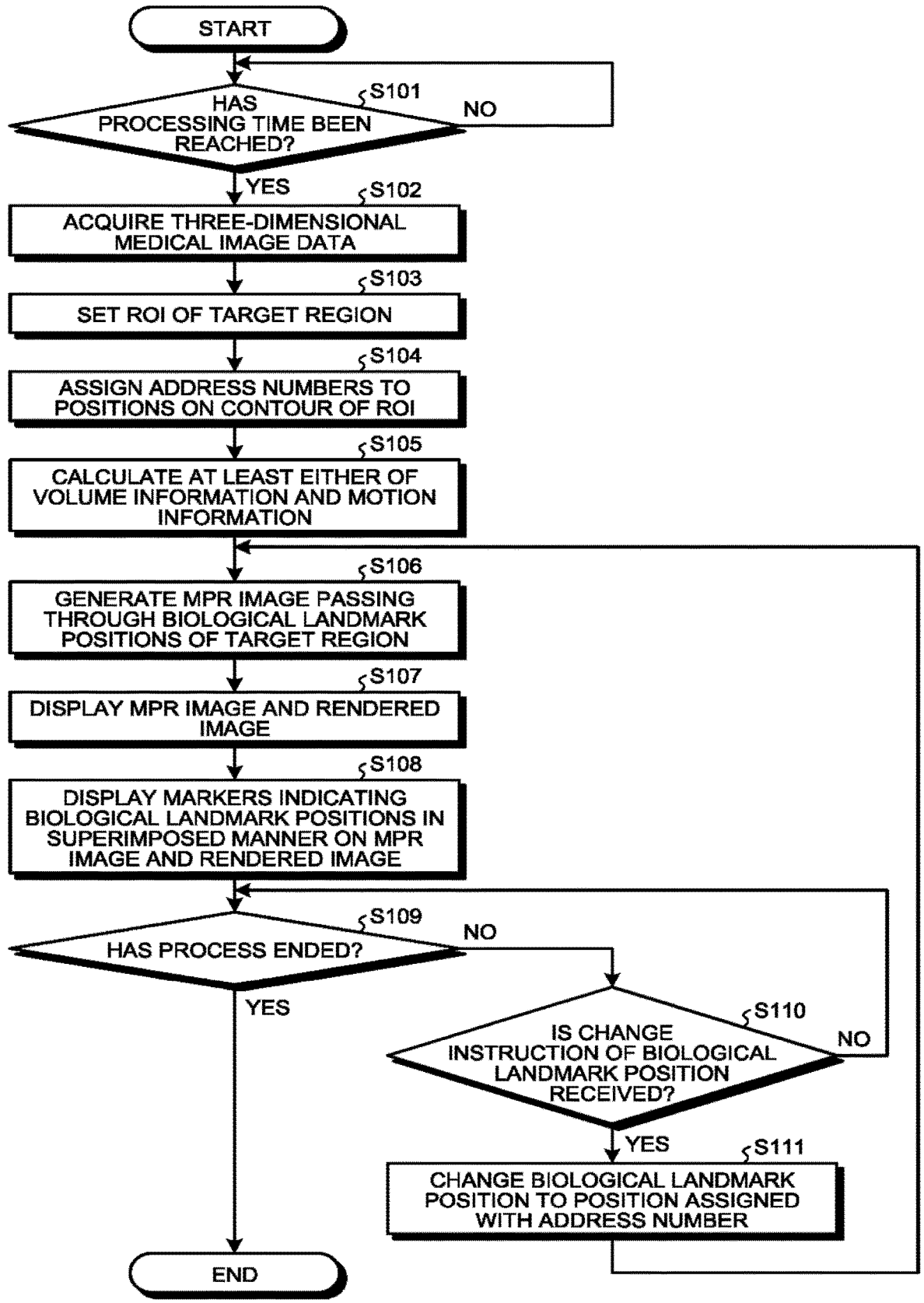
FIG. 8 is a flowchart illustrating the procedure of the ultrasonic diagnostic apparatus according to the first embodiment.

FIG. 8 is a flowchart illustrating the procedure of the ultrasonic diagnostic apparatus 1 according to the first embodiment. The procedure illustrated in FIG. 8 starts, for example, when an instruction to start analyzing the motion information is received from the operator.

At Step S101, a determination is made as to whether processing time has been reached. For example, the input device 102 receives the instruction to start analyzing the motion information from the operator, and transmits the received instruction to the processing circuitry 170. After receiving the instruction transferred from the input device 102, the processing circuitry 170 determines that the processing time has been reached (Yes at Step S101), and starts processing at Step S102 and subsequent steps. If the processing time has not been reached (No at Step S101), the processing at Step S102 and subsequent steps does not start, and the processing functions of the processing circuitry 170 stands by.

If the result of Step S101 is affirmative, the acquiring function 171 acquires the three-dimensional medical image data at Step S102. For example, the acquiring function 171 acquires the three-dimensional medical image data obtained by imaging the heart of the subject P for at least one heartbeat.

At Step S103, the ROI setting function 173 sets an ROI of a target region. For example, the ROI setting function 173 performs the segmentation of the three-dimensional medical image data, and detects the area corresponding to the right ventricle. The ROI setting function 173 sets, in the detected area, the ROI in which the dividing positions are defined by the biological landmark positions (NIB and AP positions).

At Step S104, the identification information setting function 172 assign address numbers to a plurality of positions on the contour of the ROI. For example, the identification information setting function 172 sets a plurality of track points (constituting points) assigned with address numbers in positions corresponding to the contour of the right ventricle in at least one piece of the ultrasonic image data included in the ultrasonic image data group.

At Step S105, the calculating function 174 calculates, from the three-dimensional medical image data, at least either of the volume information on the ROI and the motion information on the ROI. For example, the calculating function 174 performs the tracking process including the pattern matching using the ultrasonic image data at the initial time phase in which the constituting points are set and the ultrasonic image data at the next time phase, and thus tracks the positions of the constituting points in a plurality of pieces of the ultrasonic image data included in the ultrasonic image data group.

At Step S106, the two-dimensional image generating function 175 generates the MPR image passing through the biological landmark positions of the target region. For example, the two-dimensional image generating function 175 generates (reconstructs), from the ultrasonic image data, the MPR image data that passes through the two points of the MB and AP positions serving as the dividing positions of the ROI.

At Step S107, the output controlling function 176 displays the MPR image and the rendered image. For example, the output controlling function 176 displays the MPR image 50 based on the cross-sectional image data and the rendered image 60 generated by the rendering processing of the ultrasonic image data on the display 103. Inc output controlling function 176 converts the motion information on the respective divided regions into color codes and maps the results on the rendered image 60.

At Step S108, the output controlling function 176 displays the markers indicating the biological landmark positions in a superimposed manner on the MPR image and the rendered image. For example, the output controlling function 176 displays the MB marker 51 indicating the MB position and the AP marker 52 indicating the AP position in a superimposed manner on the MPR image 50, and displays the MB marker 61 indicating the MB position in a superimposed manner on the rendered image 60.

At Step S109, the processing circuitry 170 determines whether the process has ended. For example, the input device 102 receives an instruction to end the process from the operator, and transmits the received instruction to the processing circuitry 170. After receiving the instruction transferred from the input device 102, the processing circuitry 170 determines that the process has ended (Yes at Step S109), and ends the process of FIG. 8. If the process has not been ended (No at Step S109), the processing circuitry 170 proceeds to the processing at Step S110.

If the result of Step S109 is negative, the adjusting function 177 determines, at Step S110, whether a change instruction of a biological landmark position is received. For example, if the operator performs the drag operation to move the mark 72 of "M" rightward, the adjusting function 177 determines that the change instruction of the biological landmark position is received (Yes at Step S110), and proceeds to the processing at Step S111. If no change instruction is received (No at Step S110), the processing circuitry 170 proceeds to the processing at Step S109.

If the result of Step S110 is affirmative, the adjusting function 177 changes, at Step S111, the biological landmark position to a position assigned with an address number. For example, the adjusting function 177 moves the MB marker 61 rightward according to the rightward movement of the mark 72, and the processing of the Step S106 is performed. In other words, the two-dimensional image generating function 175 uses the biological landmark position after being adjusted to generate the cross-sectional image data. Each time the two-dimensional image generating function 175 has generated the cross-sectional image data, the output controlling function 176 displays the display image based on the updated cross-sectional image data. In this manner, each time the change instruction of the biological landmark position is received (Yes at Step S110), the processing at Steps 3106 to 3108 is repeated.

As described above, in the ultrasonic diagnostic apparatus 1 according to the first embodiment, the acquiring function 171 acquires the three-dimensional medical image data obtained by photographing a region of the subject. The ROI setting function 173 sets the ROI in the three-dimensional medical image data. The calculating function 174 calculates, from the three-dimensional medical image data, at least either of the volume information representing the volume of the ROI and the motion information representing the motion function of the ROI. The two-dimensional image generating function 175 generates, from the three-dimensional medical image data, the cross-sectional image data of the cross-section passing through the feature position representing the anatomical feature of the region. The output controlling function 176 displays a display image based on the cross-sectional image data, and outputs at least either of the volume information and the motion information corresponding to the divided regions obtained by dividing the ROI based on the feature positions. With these functions, the ultrasonic diagnostic apparatus 1 can support the correct setting of the dividing positions of the ROI in the positions representing the anatomical features.

For example, the annular structure that called the right ventricular ring (RV ring) anatomically divides the right ventricle into two regions of the inflow part and the outflow part. Accordingly, to analyze the function of the right ventricle according to, for example, the myocardial strain and the volume, the right ventricle needs to be analyzed separately for the inflow part and the outflow part. To analyze the local cardiac wall motion in more detail, it is considered to be appropriate to divide the right ventricle into the inflow part and the outflow part, and to further segment these parts. The ultrasonic diagnostic apparatus 1 according to the first embodiment sets, in the three-dimensional medical image data, the ROI in which the positions are defined by the biological landmark positions of the RV ring. As a result, the ultrasonic diagnostic apparatus 1 can easily analyze the volume information and the motion information on the two regions of the inflow part and the outflow part divided by the RV ring, and on the regions obtained by further segmenting the inflow part and the outflow part.

For example, the ultrasonic diagnostic apparatus 1 generates and displays the MPR image data passing through the biological landmark positions. As a result, the ultrasonic diagnostic apparatus 1 can always display the biological landmark positions in the MPR image. Furthermore, the ultrasonic diagnostic apparatus 1 displays the markers corresponding to the biological landmark positions. This display allows the operator to easily check whether the biological landmark positions are in the correct positions by comparing and checking the structure of the biological landmarks and the marker display positions displayed in the MPR image.

For example, the ultrasonic diagnostic apparatus 1 adjusts the biological landmark positions according to the operation performed by the operator, and uses the biological landmark positions after being adjusted to generate and display the MPR image data. As a result, the ultrasonic diagnostic apparatus 1 can adjust the biological landmark positions to positions desired by the operator. Specifically, the operator can check the MPR image updated according to the adjustment of the biological landmark positions and the markers displayed corresponding to the biological landmark positions even if the biological landmark positions in an image of subject data entered vary from person to person, and thus can set the marker display positions so as to coincide with the appropriate structural positions of the biological landmarks in the MPR image. This allows the operator to determine appropriate landmark positions even if the biological landmark positions vary from person to person.

In the embodiment above, the case has been described where the MB and AP positions are used as the biological landmark positions. The embodiments are, however, not limited to this case. For example, a case can be considered where the ultrasonic diagnostic apparatus 1 uses either of the MB and AP positions as a biological landmark position.

Other Embodiments

The present embodiment may be carried out in various embodiments in addition to the embodiment described above.

Clear Indication of Movable Directions of Biological Landmark Positions

Figure 9:
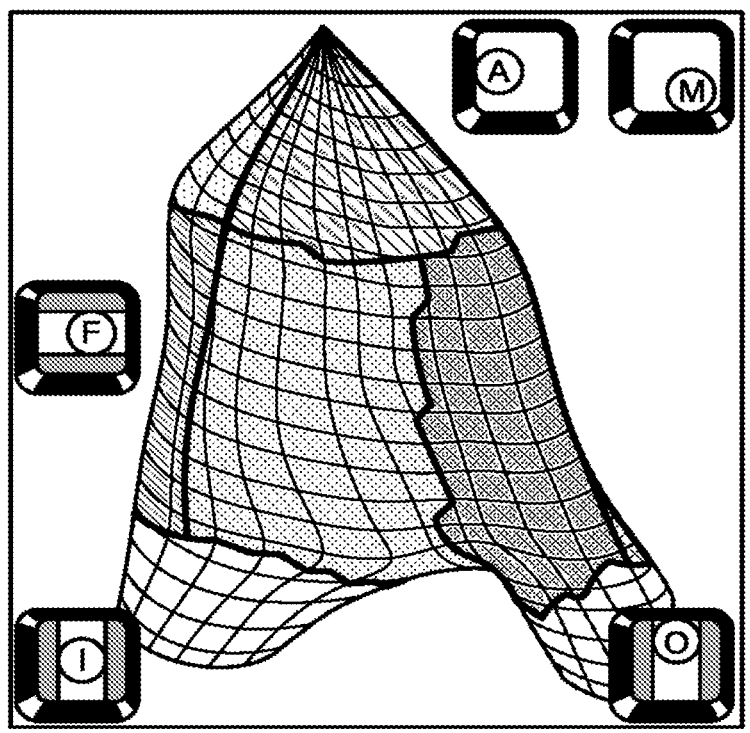
FIG. 9 is a diagram for explaining processing of the adjusting function according to another embodiment.

For example, the ultrasonic diagnostic apparatus 1 may clearly indicate the movable directions of the biological landmark positions. FIG. 9 is a diagram for explaining processing of the adjusting function 177 according to another embodiment. FIG. 9 illustrates the rendered image displayed on the display 103 by the output controlling function 176. In addition to the icon 70 of "A" and the icon 71 of "M" illustrated in FIG. 7A, an icon of "F", an icon of "I", and an icon of "O" are displayed in the rendered image of FIG. 9. The icon of "F" is an icon for changing the boundary position between the lateral wall side inflow part (RVIT Lat) and the inferior wall side inflow part (RVIT Inf) of the free wall in the right-left direction (circumferential direction). The icon of "I" is an icon for changing the lower end position (tricuspid level) of the inflow part of the right ventricle in the up-down direction (long axis direction). The icon of "O" is an icon for changing the lower end position (pulmonary valve level) of the outflow part of the right ventricle in the up-down direction (long axis direction).

As illustrated in FIG. 9, the icon of "F" is divided into three regions in the up-down direction. The top and bottom regions of the three regions are indicated in gray. The gray regions are indicated as regions into which the "F" mark is not movable. In other words, the "F" mark in the icon of "F" is indicated to be not movable in the up-down direction and movable only in the right-left direction.

Each of the icons of "I" and "O" is divided into three regions in the right-left direction. The right and left regions of the three regions are indicated in gray. That is, the "I" and "O" marks in the icons of "I" and "O", respectively, are indicated to be not movable in the right-left direction and movable only in the up-down direction.

In this manner, the adjusting function 177 can provide icons, such as the icons of "F", "I", and "O", indicating the movable directions of the respective biological landmark positions, for the operator.

Dynamic-MPR Display

For example, the ultrasonic diagnostic apparatus 1 may use the processing described above to perform Dynamic-MPR display.

For example, the acquiring function 171 acquires a plurality of pieces of three-dimensional medical image data obtained by imaging a region in chronological order. The two-dimensional image generating function 175 generates, from each of the pieces of three-dimensional medical image data, cross-sectional image data passing through feature positions in the piece of three-dimensional medical image data. The output controlling function 176 displays, in chronological order, the pieces of cross-sectional image data generated from the respective pieces of three-dimensional medical image data.

For example, the biological landmark positions are associated across all time phases by the tracking process described above. Hence, the two-dimensional image generating function 175 identifies the biological landmark positions in each of the pieces of ultrasonic image data included in the ultrasonic image data group in chronological order. For the biological landmark positions identified in each of the pieces of ultrasonic image data, the two-dimensional image generating function 175 generates an MPR image passing through the biological landmark positions in the piece of ultrasonic image data. The output controlling function 176 displays, in chronological order, the respective MPR images thus generated. As a result, the ultrasonic diagnostic apparatus 1 can provide a moving image of the MPR images passing through the biological landmark positions that dynamically change in chronological order.

MPR Display with Thickness

For example, the ultrasonic diagnostic apparatus 1 may generate and display an MPR image passing through the biological landmark positions as an MPR image with thickness.

For example, the two-dimensional image generating function 175 generates, from the three-dimensional medical image data, cross-sectional image data with thickness serving as image data of a cross-section that passes through the feature positions and that has a predetermined thickness. Specifically, the two-dimensional image generating function 175 obtains the average value of luminance values within a thickness (in a direction orthogonal to the MPR cross-section) based on a set value of, for example, 5 mm, and reconstructs the MPR image. This approach increases the frequency at which the displayed MPR image includes signals in the biological landmark positions, and thereby makes it easy to determine the biological landmark positions at the time of searching for the correct biological landmark positions.

Hiding of Markers in Rendered Image

In the embodiment above, a case has been described, for example, of displaying the MB marker 61 in the rendered image 60. The embodiments are, however, not limited to this case. The MB marker 61 need not be displayed. Also in this case, the operator can determine the validity of the biological landmark positions by checking the MB and AP positions represented in the MPR image 50. If the biological landmark positions are adjustable, the operator can search for positions considered to be correct by changing the biological landmark positions. In this case, each of the biological landmark positions is preferably configured to be changed by one address at a tune. Specifically, after receiving an operation of pressing an arrow key of up, down, right, or left while keeping pressing the "M" key on the keyboard, the adjusting function 177 moves the MB position by one address in a direction corresponding to the arrow key; or, after receiving an operation of pressing an arrow key of up, down, right, or left while keeping pressing the "A" key on the keyboard, the adjusting function 177 moves the MB position by one address in a direction corresponding to the arrow key. In this manner, the ultrasonic diagnostic apparatus 1 makes it easy to search for the correct biological landmark positions by moving each of the biological landmark positions by one address at a time without the need for displaying the markers in the rendered image.

Display of Three-Dimensional ROI Using Polar Map

Examples have been described above in which the (surface) rendered image 60 is used as a way of display that allows the operator to three-dimensionally view the MB and AP positions. As another way of display that allows the operator to view a state of the entire three-dimensional ROI in one view, a display using a polar map widely known to be applied to the left ventricle may be applied to the right ventricle. In this case, the MB and AP markers are preferably displayed in positions corresponding to the MB and AP positions in the polar map configured for the right ventricle.

The components of the devices illustrated in the drawings are functionally conceptual, and need not be physically configured as illustrated. In other words, the specific mode of dispersion and integration of the devices is not limited to those illustrated in the drawings, and all or some of the devices can be configured in a functionally or physically dispersed or integrated manner in any units according to various types of loads or use conditions. Furthermore, all or any part of the processing functions performed in the devices can be implemented by a CPU and program analyzed and executed by the CPU, or can be implemented as hardware with a wired logic.

Of the processes described in the embodiments above, all or some of the processes described to be automatically performed can also be manually performed, and all or some of the processes described to be manually performed can also be automatically performed using a known method. In addition, the processing procedures, the control procedures, the specific names, and the information including various types of data and parameters illustrated in the above description and the drawings can be freely modified unless otherwise specified.

The medical image processing method described in each of the embodiments above can be performed by executing a medical image processing program provided in advance on a computer, such as a personal computer or a workstation. The medical image processing method can be distributed through a network, such as the Internet. The medical image processing method can also be executed by being recorded on a computer-readable recording medium, such as a hard disk, a flexible disk (FD), a compact disc read-only memory (CD-ROM), a magneto-optical (MO) disk, or a digital versatile disc (DVD), and by being read by a computer from the recording medium.

In other words, an image processing apparatus can execute what has been described in the embodiments above. For example, the image processing apparatus includes the acquiring unit, the calculating unit, the ROI setting unit, the image generating unit, and the output controlling unit. The acquiring unit acquires the time-series volume data obtained by imaging the region of the subject in motion. The calculating unit uses the volume data and performs processing including the tracking to calculate at least either of the volume information and the motion information on the ROI of the subject. The ROI setting unit sets one or more feature positions that represent anatomical features in the ROI. The image generating unit generates the MPR image that passes through at least one of the feature positions. The output controlling unit displays the MPR image, and outputs at least either of the volume information and the motion information that includes the feature positions as boundaries.

What has been described in the embodiments above can be performed as an image processing method. For example, the image processing method includes acquiring the time-series volume data obtained by imaging the region of the subject in motion, includes calculating at least either of the volume information and the motion information on the ROI of the subject by performing processing including the tracking using the volume data, includes setting one or more feature positions that represent anatomical features in the ROI, includes generating the MPR image that passes through at least one of the feature positions, and includes displaying the MPR image and outputting at least either of the volume information and the motion information that includes the feature positions as boundaries.

According to at least one of the embodiments described above, a region of a subject can be analyzed for each area of the region divided based on positions representing anatomical features.

While certain embodiments have been described, these embodiments have been presented by way of example only, and are not intended to limit the scope of the inventions. Indeed, the novel embodiments described herein may be embodied in a variety of other forms; furthermore, various omissions, substitutions and chances in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
an ultrasonic probe configured to collect reflected wave data in a time series manner from a region including a heart of a subject in motion; and
processing circuitry configured to:
generate time-series volume data from the reflected wave data collected by the ultrasonic probe,
set a region of interest (ROI) in an area corresponding to a right ventricle of the heart included in the volume data,
set identification information identifying each of a plurality of positions representing a contour of the region in the volume data,
calculate at least either of volume information and motion information on the ROI by performing processing including tracking using the volume data, set positions in the ROI as feature positions among the plurality of positions, the feature positions being positions on a three-dimensional ring shaped boundary between an inflow part and an outflow part of the right ventricle, and being at least two positions of a position of an anterior papillary muscle of the right ventricle, a position where a trabecula septomarginalis of the right ventricle shifts to a moderator band, and a position of a crista supraventricularis of the right ventricle, adjust, from among the positions on which the identification information has been set, a feature position of the feature positions corresponding to at least one of the position of the anterior papillary muscle of the right ventricle and the position where the trabecula septomarginalis of the right ventricle shifts to the moderator band, according to an operation performed by an operator, generate a multiplanar reconstruction (MPR) image that passes through the at least two feature positions, display the MPR image, output at least either of the volume information and the motion information that includes the feature positions as boundaries, regenerate the MPR image using the adjusted feature position after being adjusted, each time the adjusted feature position has been adjusted, and display the regenerated MPR image each time the MPR image has been regenerated, wherein the processing circuitry is further configured to:
display a rendered image based on the volume data, and display first markers that indicate the feature positions in the rendered image, the feature positions corresponding to at least one of the position of the anterior papillary muscle of the right ventricle and the position where the trabecula septomarginalis of the right ventricle shifts to the moderator band, and output at least either of the volume information and the motion information on each of a plurality of divided regions obtained by dividing the ROI with boundary lines passing through the feature positions, the feature positions corresponding to at least one of the position of the anterior papillary muscle of the right ventricle and the position where the trabecula septomarginalis of the right ventricle shifts to the moderator band.

2. The ultrasonic diagnostic apparatus according to claim 1, wherein the processing circuitry is configured to receive, from the operator, an operation specifying a direction and a distance of moving the feature position in a rendered image based on the volume data, and to adjust the feature position according to the direction and the distance.

3. The ultrasonic diagnostic apparatus according to claim 2, wherein the processing circuitry is configured to display an image representing movable directions of the feature position, and to receive, from the operator, the operation specifying the direction and the distance via the image.

4. The ultrasonic diagnostic apparatus according to claim 1, wherein the processing circuitry is configured to display second markers that indicate the feature positions in the MPR image.

5. The ultrasonic diagnostic apparatus according to claim 1, wherein the processing circuitry is configured to output at least either of the volume information and the motion information on each of a plurality of divided regions obtained by further dividing, with boundary lines not passing through the feature positions, the divided regions obtained by dividing the ROI with the boundary lines passing through the feature positions.

6. The ultrasonic diagnostic apparatus according to claim 1, wherein the processing circuitry is configured to:
generate a plurality of pieces of volume data obtained by imaging the region in chronological order,
generate, from each of the pieces of volume data, the MPR image passing through the feature positions in the piece of volume data, and
display, in chronological order, the MPR image generated from each of the pieces of volume data.

7. The ultrasonic diagnostic apparatus according to claim 1, wherein the processing circuitry is configured to generate, from the volume data, an MPR image with thickness that passes through the feature positions and that has a predetermined thickness.

8. An image processing apparatus comprising:
processing circuitry configured to:
acquire time-series volume data obtained by imaging a region including a heart of a subject in motion,
set a region of interest (ROI) in an area corresponding to a right ventricle of the heart included in the volume data,
set identification information identifying each of a plurality of positions representing a contour of the region in the volume data,
calculate at least either of volume information and motion information on the ROI by performing processing including tracking using the volume data,
set positions in the ROI as feature positions among the plurality of positions, the feature positions being positions on a three-dimensional ring shaped boundary between an inflow part and an outflow part of the right ventricle, and being at least two positions of a position of an anterior papillary muscle of the right ventricle, a position where a trabecula septomarginalis of the right ventricle shifts to a moderator band, and a position of a crista supraventricularis of the right ventricle,
adjust, from among the positions on which the identification information has been set, a feature position of the feature positions corresponding to at least one of the position of the anterior papillary muscle of the right ventricle and the position where the trabecula septomarginalis of the right ventricle shifts to the moderator band, according to an operation performed by an operator,
generate a multiplanar reconstruction (MPR) image that passes through the at least two feature positions, display the MPR image,
output at least either of the volume information and the motion information that includes the feature positions as boundaries,
regenerate the MPR image using the adjusted feature position after being adjusted, each time the adjusted feature position has been adjusted, and
display the regenerated MPR image each time the MPR image has been regenerated, wherein
the processing circuitry is further configured to:
display a rendered image based on the volume data, and display first markers that indicate the feature positions in the rendered image, the feature positions corresponding to at least one of the position of the anterior papillary muscle of the right ventricle and the position where the trabecula septomarginalis of the right ventricle shifts to the moderator band, and output at least either of the volume information and the motion information on each of a plurality of divided regions obtained by dividing the ROI with boundary lines passing through the feature positions, the feature positions corresponding to at least one of the position of the anterior papillary muscle of the right ventricle and the position where the trabecula septomarginalis of the right ventricle shifts to the moderator band.

9. An image processing method comprising:
acquiring, by processing circuitry, time-series volume data obtained by imaging a region including a heart of a subject in motion;
setting, by the processing circuitry, a region of interest (ROI) in an area corresponding to a right ventricle of the heart included in the volume data;
setting, by the processing circuitry, identification information identifying each of a plurality of positions representing a contour of the region in the volume data;
calculating, by the processing circuitry, at least either of volume information and motion information on the ROI by performing processing including tracking using the volume data;
setting, by the processing circuitry, positions in the ROI as feature positions among the plurality of positions, the feature positions being positions on a three-dimensional ring shaped boundary between an inflow part and an outflow part of the right ventricle, and being at least two positions of a position of an anterior papillary muscle of the right ventricle, a position where a trabecula septomarginalis of the right ventricle shifts to a moderator band, and a position of a crista supraventricularis of the right ventricle;
adjusting, by the processing circuitry, from among the positions on which the identification information has been set, a feature position of the feature positions corresponding to at least one of the position of the anterior papillary muscle of the right ventricle and the position where the trabecula septomarginalis of the right ventricle shifts to the moderator band, according to an operation performed by an operator;
generating, by the processing circuitry, a multiplanar reconstruction (MPR) image that passes through the at least two feature positions;
displaying, by the processing circuitry, the MPR image and outputting at least either of the volume information and the motion information that includes the feature positions as boundaries;
regenerating the MPR image using the adjusted feature position after being adjusted, each time the adjusted feature position has been adjusted;
displaying the regenerated MPR image each time the MPR image has been regenerated;
displaying a rendered image based on the volume data, and displaying first markers that indicate the feature positions in the rendered image, the feature positions corresponding to at least one of the position of the anterior papillary muscle of the right ventricle and the position where the trabecula septomarginalis of the right ventricle shifts to the moderator band; and
outputting at least either of the volume information and the motion information on each of a plurality of divided regions obtained by dividing the ROI with boundary lines passing through the feature positions, the feature positions corresponding to at least one of the position of the anterior papillary muscle of the right ventricle and the position where the trabecula septomarginalis of the right ventricle shifts to the moderator band.

* * * * *